United States Patent
Hirota et al.

[11] Patent Number: 6,028,076
[45] Date of Patent: Feb. 22, 2000

[54] PURINE DERIVATIVE

[75] Inventors: Kohsaku Hirota, Gifu; Yoshiaki Isobe; Nobuyoshi Chiba, both of Saitama; Harumi Satoh, Tokyo; Haruo Takaku, Saitama; Hiroyuki Matsui, Saitama; Haruhisa Ogita, Saitama, all of Japan

[73] Assignee: Japan Energy Corporation, Tokyo, Japan

[21] Appl. No.: 09/029,076

[22] PCT Filed: Jul. 3, 1997

[86] PCT No.: PCT/JP97/02310

§ 371 Date: Mar. 3, 1998

§ 102(e) Date: Mar. 3, 1998

[87] PCT Pub. No.: WO98/01448

PCT Pub. Date: Jan. 15, 1998

[30] Foreign Application Priority Data

Jul. 3, 1996 [JP] Japan ..................... 8-173857

[51] Int. Cl.[7] ............... A61K 31/52; C07D 473/34; C07D 473/30; C07D 473/00; C07D 473/38
[52] U.S. Cl. ................ 514/262; 544/265; 544/276; 544/277
[58] Field of Search ................ 544/277, 276, 544/265; 514/261, 262, 266

[56] References Cited

U.S. PATENT DOCUMENTS

| 5,117,830 | 6/1992 | McAfee | 128/654 |
| 5,256,398 | 10/1993 | McAfee | 424/9 |

FOREIGN PATENT DOCUMENTS

| 1220148 | 4/1987 | Canada . |
| 0 545 413 | 6/1993 | European Pat. Off. . |
| 46-39716 | 11/1971 | Japan . |
| 47-8547 | 3/1972 | Japan . |
| 47-26514 | 7/1972 | Japan . |
| 4-503506 | 4/1992 | Japan . |
| 50-22039 | 7/1995 | Japan . |
| 95/00439 | 1/1995 | WIPO . |
| WO 96/26208 | 8/1996 | WIPO . |

OTHER PUBLICATIONS

Holy, Coll. Czech Chem Comm 48, 1910, 1983.
Abstract for Yokochi, Arzneimittelforschung 47, 968, 1997.
Abstract for Balachandra, Southeast Asian I. Trop Med Pub Health 25, 252, Jun. 1994.
Abstract for Pawlotsky, J. Interferon Cytokine Res 15,857, Oct. 1995.
Abstract for Berthillon, J. Hepatol 25, 15, Jul. 1996.
Abstract for Lanford, Virology 202, 606, Aug. 1994.
Abstract for Ilan, J. Infect Dis 166, 1164, Nov. 1992.
Abstract for Degre, Acta Pathol Microbiol Scan(B) 88, 177, Jun. 1980.
Abstract for Shibata, Jpn J. CLin Oncol 15, 67, Mar. 1985.
Abstract for Shimoyama, Gan No Rinsho 29, 589, May 1983.
Abstract for Kamihira, Gan To Kagaku Ryoho 10, 2188, Oct. 1983.
Abstract for Nickoloff, J. Inves Dermatol 84, 487, Jun. 1985.
Abstract for Kuebler, Inves New Drugs 5 21, Jan. 1987.
Abstract for Roth, Am. J. Med 81, 871, Nov. 1986.
Abstract for Balmer, Drug Intell Clin Pharm 19, 887, Dec. 1985.
Abstract for Jacobs, Blood 65, 1017, Apr. 1985.
Abstract for Saigo, Blut 56, 83, Feb. 1988.
Abstract for Hara, Nippon, Hinyokika Gakkai Zasshi 80, 158, Feb. 1989.
Kelley, J Med Chem 33, 196 (1990).
Fujii, Chem Pharm Bull 38(6) 2146 (1990).
Holy, CA 90, 121544 (1978).
Holy CA 113, 41170 (1990).
Rahat, JCS Perkins I, 2229, 1974.
Yoneda, JCS Perkins I, 2285, 1977.
Saito, Chem Pharm Bull 41(10) 1746, 1993.
Calmane, Chem Abs 114, 7056d, 1990.
Ikehara, Chem Abs 78, 148193w, 1973.
Altman, J. Het Chem 5(5) p 679, Oct. 1968.

*Primary Examiner*—Mark L. Berch
*Attorney, Agent, or Firm*—Oblon, Spivak, McClelland, Maier & Neustadt, P.C.

[57] ABSTRACT

This invention relates to novel purine derivatives of formula (I):

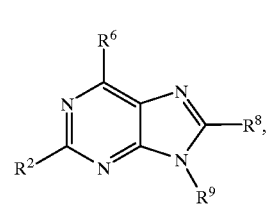

where $R^2$ and $R^9$ are hydrocarbon groups, $R^6$ is an amino group and $R^8$ is a hydroxyl, or acyloxy group. These purine derivatives are effective at promoting secretion of interferon in patients, and can be used to treat diseases against which interferon is effective.

5 Claims, No Drawings

PURINE DERIVATIVE

This application is a 371 of PCT Application PCT/JP9702310, filed on Jul. 3, 1997, which claims priority to Japanese Application Serial No. 8/173857, filed Jul. 3, 1996.

TECHNICAL FIELD

The present invention relates to a purine derivative or pharmaceutically acceptable salts thereof which are useful for treatment of cancer or viral diseases such as type B hepatitis, type C hepatitis or AIDS; and to an interferon inducer, an anti-virus agent and an anti-cancer agent which comprise said purine derivative as an active ingredient.

BACKGROUND ART

Interferon is one of the most important factors in defense against infections and regulation of immunity, and it has been used for treatment of type B and type C hepatitis and for immunotherapy of cancer. Interferon is actually the sole drug against type C hepatitis. Because interferon is a polypeptide having a molecular weight of about 20,000, it can be applied only by injection and its neutralizing antibody may arise. Since main object of interferon therapy is chronic diseases, there are clinical problems such as restriction of quality of life by long-period going to hospital and decrease of the effect caused by the generation of neutralizing antibody for interferon. Accordingly, orally applicable interferon inducers are desired.

Double-strand nucleic acids originating from virus or other organisms and high molecular polymers such as poly(I):poly(C) and polycarboxylates have been known as interferon inducers. However, their antigenicity, pollution by pathogens, and biological instability are worried, it is therefore difficult to develop high molecular polymers as oral drugs. Fluorenones, pyrimidinones, and anthraquinones have been studied as low-molecular interferon inducers [Mayer, G. D., et al.: Science, 1970, 169, 1214; Nichol, F. R., et al.: Antimicrob. Agents Chemother., 1976, 9, 433; Stringfellow, D. A., et al.: Antimicrob. Agents Chemother., 1991, 15, 111]. However, their development was abandoned because of their insufficient effect or their toxicity [Reiter, M. A., et al.: J. Leukocyte Biol., 1994, 55, 234]. Although imidazoquinolines are known as low-molecular interferon inducers [EP 145,340], they have a low selectivity to interferon and also induce other cytokines, especially TNF-α and IL-6.

DISCLOSURE OF INVENTION

The object of the present invention is to provide an interferon inducer, an anti-virus agent, and an anti-cancer agent comprising, as an active ingredient, a low-molecular compound without antigenicity which is orally applicable for treatment of cancer and viral diseases, such as type B and type C hepatitis and AIDS.

The inventors now found that purine derivatives having a specific structure show selective and potent activity of interferon induction, and completed the present invention.

The present invention is a purine derivative represented by the following general formula (I):

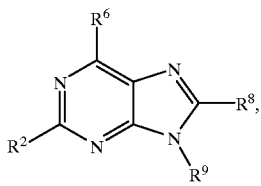

(I)

wherein
R$^2$ is a hydrogen atom or a hydrocarbon group containing at most 14 carbon atoms; any —CH$_2$— group in said hydrocarbon group may be replaced with a carbonyl group, a sulfonyl group, —O— or —S— when said —CH$_2$— group is not directly attached to the purine ring or is in —CH$_3$ group not directly attached to the purine ring; any =CH$_2$ group may be replaced with =O or =S; C—H group in said hydrocarbon group may be replaced with N, a C-halogen group or a C—CN group when said C—H group is in —CH$_2$— group not directly attached to the purine ring, in —CH$_3$ group not directly attached to the purine ring, in >CH— group not directly attached to the purine ring, in =CH— group not directly attached to the purine ring or in =CH$_2$ group;

R$^6$ is a hydroxyl group, an amino group or an amino group mono- or di-substituted with a hydrocarbon group containing at most 10 carbon atoms;

R$^8$ is a hydroxyl group, a mercapto group, an acyloxy group containing at most 18 carbon atoms or an oxycarbonyloxy group substituted with a hydrocarbon group containing at most 19 carbon atoms;

R$^9$ is a hydrocarbon group containing at most 14 carbon atoms; any —CH$_2$— group in said R$^9$ may be replaced with a carbonyl group, a sulfonyl group, —O— or —S— when said —CH$_2$— group is not directly attached to the purine ring or is in —CH$_3$ group not directly attached to the purine ring; any =CH$_2$ group may be replaced with =O or =S; C—H group in said R$^9$ may be replaced with N, a C-halogen group or a C—CN group when said C—H group is in —CH$_2$— group not directly attached to the purine ring, in —CH$_3$ group not directly attached to the purine ring, in >CH— group not directly attached to the purine ring, in =CH— group not directly attached to the purine ring, in =CH$_2$ group or in ≡CH group;

or its tautomer or pharmaceutically acceptable salts thereof, and an interferon inducer, an anti-virus agent or an anti-cancer agent which comprises said purine derivative or pharmaceutically acceptable salts thereof as an active ingredient.

The compound of the present invention is described in detail below.

The hydrocarbon group of R$^2$ containing at most 14 carbon atoms includes a linear or branched chain hydrocarbon group, a monocyclic hydrocarbon group with or without side chain, a polycyclic hydrocarbon group with or without side chain, a spiro hydrocarbon group with or without side chain, a ring-assembling structural hydrocarbon group with or without side chain, or a chain hydrocarbon group substituted with said cylcic hydrocarbon groups. It includes any saturated or unsaturated hydrocarbon group, provided that unsaturated hydrocarbon groups having salline structure (C=C=C) are excluded. The linear or branched chain hydrocarbon group includes, for example, saturated chain hydrocarbon groups such as a linear alkyl group containing at least one carbon atom and a branched alkyl group containing at least three carbon atoms; unsaturated chain hydrocarbon groups such as a linear alkenyl group containing at least two carbon atoms, a branched alkenyl group containing at least three carbon atoms, a linear alkynyl group containing at least three carbon atoms, a branched alkynyl group containing at least four carbon atoms, a linear alkadienyl group containing at least four carbon atoms and a branched alkadienyl group containing at least five carbon atoms. The monocyclic hydrocarbon group includes, for example, saturated monocyclic hydrocarbon groups such as a cycloalkyl group without side chain which contains at least three carbon atoms and a cycloalkyl group with side chain which contains at least four carbon atoms in total; unsaturated monocyclic hydrocarbon groups such as a cycloalkenyl group without side chain which contains at least four carbon atoms, a cycloalkynyl group with side chain which contains at least five carbon atoms in total, a cycloalkadienyl group without side chain which contains at least five carbon atoms and a cycloalkadienyl group with side chain which contains at least six carbon atoms in total. The aromatic hydrocarbon group includes an aromatic group without side chain which contains 6 to 14 carbon atoms in total such as phenyl group, 1-naphthyl group, 2-naphthyl group and 9-anthryl group; an aromatic group with side chain which contains at least seven carbon atoms in total; phenylphenyl group containing 12 carbon atoms and phenylphenyl group with side chain which contains at least 13 carbon atoms in total which phenylphenyl groups are also included in a ring-assembling structural hydrocarbon group. The polycyclic hydrocarbon group includes a condensed cyclic hydrocarbon group without side chain which contains at least six carbon atoms, a condensed cyclic hydrocarbon group with side chain which contains at least seven carbon atoms in total, a bridged cyclic hydrocarbon group without side chain which contains at least seven carbon atoms, a bridged cyclic hydrocarbon group with side chain which contains at least eight carbon atoms in total, a spiro hydrocarbon group without side chain which contains at least nine carbon atoms in total and a spiro hydrocarbon group with side chain which contains at least 10 carbon atoms in total. In addition, said condensed cyclic hydrocarbon group without side chain includes those which contain at least nine carbon atoms in total when one of its condensed rings is benzene ring, and said condensed cyclic hydrocarbon group with side chain includes those which contain at least 10 carbon atoms in total when one of its condensed rings is benzene ring. The ring-assembling structural hydrocarbon group includes a cycloalkyl-cycloalkyl group without side chain which contains at least six carbon atoms in total, a cycloalkyl-cycloalkyl group with side chain which contains at least seven carbon atoms in total, a cycloalkylidene-cycloalkyl group without side chain which contains at least six carbon atoms in total and a cycloalkylidene-cycloalkyl group with side chain which contains at least seven carbon atoms in total. "A cyclic hydrocarbon with side chain" corresponds to one substituted with chain hydrocarbon group or groups on its ring. The chain hydrocarbon group substituted with said cyclic hydrocarbon groups includes a linear alkyl group which is substituted with an aromatic group without side chain and contains at least seven carbon atoms in total, a linear alkyl group which is substituted with an aromatic group with side chain and contains at least eight carbon atoms in total, a branched alkyl group which is substituted with an aromatic group without side chain and contains at least nine carbon atoms in total, a branched alkyl group which is substituted with an aromatic group with side chain and contains at least 10 carbon atoms in total, a linear alkenyl group which is substituted with an aromatic group without side chain and contains at least eight carbon atoms in total, a linear alkenyl group which is substituted with an aromatic group with side chain and contains at least nine carbon atoms in total, a branched alkenyl group which is substituted with an aromatic group without side chain and contains at least nine carbon atoms in total, a branched alkenyl group which is substituted with an aromatic group with side chain and contains at least 10 carbon atoms in total, a linear alkynyl group which is substituted with an aromatic group without side chain and contains at least eight carbon atoms in total, a linear alkynyl group which is substituted with an aromatic group with side chain and contains at least nine carbon atoms in total, a branched alkynyl group which is substituted with an aromatic group without side chain and contains at least 10 carbon atoms in total, a branched alkynyl group which is substituted with an aromatic group with side chain and contains at least 11 carbon atoms in total, a linear alkadienyl group which is substituted with an aromatic group without side chain and contains at least 10 carbon atoms in total, a linear alkadienyl group which is substituted with an aromatic group with side chain and contains at least 11 carbon atoms in total, a branched alkadienyl group which is substituted with an aromatic group without side chain and contains at least 11 carbon atoms in total, a branched alkadienyl group which is substituted with an aromatic group with side chain and contains at least 12 carbon atoms in total, a linear alkyl group which is substituted with a cycloalkyl group without side chain and contains at least four carbon atoms in total, a linear alkyl group which is substituted with a cycloalkyl group with side chain and contains at least five carbon atoms in total, a branched alkyl group which is substituted with a cycloalkyl group without side chain and contains at least six carbon atoms in total, a branched alkyl group which is substituted with a cycloalkyl group with side chain and contains at least seven carbon atoms in total, a linear alkenyl group which is substituted with a cycloalkyl group without side chain and contains at least five carbon atoms in total, a linear alkenyl group which is substituted with a cycloalkyl group with side chain and contains at least six carbon atoms in total, a branched alkenyl group which is substituted with a cycloalkyl group without side chain and contains at least six carbon atoms in total, a branched alkenyl group which is substituted with a cycloalkyl group with side chain and contains at least seven carbon atoms in total, a linear alkynyl group which is substituted with a cycloalkyl group without side chain and contains at least five carbon atoms in total, a linear alkynyl group which is substituted with a cycloalkyl group with side chain and contains at least six carbon atoms in total, a branched alkynyl group which is substituted with a cycloalkyl group without side chain and contains at least seven carbon atoms in total, a branched alkynyl group which is substituted with a cycloalkyl group with side chain and contains at least eight carbon atoms in total, a branched alkadienyl group which is substituted with a cycloalkyl group without side chain and contains at least eight carbon atoms in total, a branched alkadienyl group which is substituted with a cycloalkyl group with side chain and contains at least nine carbon atoms in total.

When $R^2$ is an aromatic group without side chain, an aromatic group with side chain, phenylphenyl group or phenylphenyl group with side chain, it refers to an aryl group, and a linear or branched alkyl group substituted with the aryl group or groups refers to an aralkyl group. Other cyclic hydrocarbon groups including both of one having side chains on their ring and one having no side chain simply refer to, for example, cycloalkyl groups, unless otherwise mentioned. Further, chain hydrocarbon groups including both of linear one and branched one simply refer to, for example, alkyl groups.

When —CH$_2$— in said hydrocarbon group is replaced with a carbonyl group, sulfonyl group, —O— or —S—, ketone, sulfone, ether or thioether structure is introduced thereinto, respectively. When —CH$_2$— in —CH$_3$ is replaced with a carbonyl group, —O— or —S—, it converts into formyl (aldehyde) group, hydroxyl group or mercapto group, respectively. When a terminal =CH$_2$ is replaced with =O or =S, ketone or thioketone is introduced thereinto. When C—H in —CH$_2$— is replaced with N, it converts into —NH—. When C—H in >CH— is replaced with N, it converts into >N—. When C—H in =CH— is replaced with N, it converts into =N—. When C—H in a terminal —CH$_3$ is replaced with N, —NH$_2$ is introduced thereinto. When C—H in =CH$_2$ is replaced with N, it converts into =NH. When C—H in C≡CH is replaced with N, it converts into cyano group (C≡N). Further, C—H in —CH$_3$, —CH$_2$—, =CH—, ≡CH or >CH— is replaced with a C-halogen group or a C—CN group, said carbon is substituted with halogeno group or cyano group. The replacement of carbon chains with —O—, —S— or N corresponds to oxa-, thia- or aza-substitution of said hydrocarbon group, respectively. For example, when these substitution take place in a ring carbon of the hydrocarbon ring, the hydrocarbon ring converts into a heterocyclic ring respectively containing oxygen, sulfur or nitrogen. The replacement of CH$_2$ and C—H in said hydrocarbon group may independently take place and it may further take place when CH$_2$ or C—H still remains on said carbon after the prior replacement. Further, these replacement may bring conversions such as conversion of —CH$_2$—CH$_2$— into —CO—O— (ester structure) and —CO—S— (thioester structure); conversion of —CH$_2$—CH$_2$—CH$_2$— into —O—CO—O— (carbonate structure) and —NH—CO—NH (urea ester structure); and conversion of —CH$_2$—CH$_3$ into —CO—O—H (carboxylic acid structure), —CO—NH$_2$(amide structure) and —SO$_2$—NH$_2$ (sulfonamide structure). The halogen includes fluorine, chlorine, bromine and iodine, particularly fluorine, chlorine and bromine being preferred.

Accordingly, the hydrocarbon group of R$^2$ containing at most 14 carbon atoms may be selected from any chain hydrocarbon group and ring-structural hydrocarbon group such as cyclic hydrocarbon groups, for example, saturated chain hydrocarbon groups such as linear or branched alkyl groups; unsaturated chain hydrocarbon groups such as linear or branched alkenyl groups, linear or branched alkynyl groups and linear or branched alkadienyl groups; saturated cyclic hydrocarbon groups such as cycloalkyl groups; unsaturated cyclic hydrocarbon groups such as cycloalkenyl groups, cycloalkynyl groups and cycloalkadienyl groups; and aromatic hydrocarbon groups such as aryl groups, aralkyl groups and arylalkenyl groups.

In more detail, the linear or branched alkyl groups include methyl group, ethyl group, propyl group, isopropyl group, butyl group, 1-methylpropyl group, pentyl group, 1-methylbutyl group, hexyl group, 1-methylpentyl group, heptyl group, 1-methylhexyl group, 1-ethylpentyl group, octyl group, nonyl group, decyl group, undecyl group, dodecyl group, tridecyl group, tetradecyl group, 2-methylpropyl group, 2-methylbutyl group, 3-methylbutyl group, 2-methylpentyl group, 3-methylpentyl group, 4-methylpentyl group, methylhexyl group, methylheptyl group, methyloctyl group, methylnonyl group, 1,1-dimethylethyl group, 1,1-dimethylpropyl group, 2,6-dimethylheptyl group, 3,7-dimethyloctyl group and 2-ethylhexyl group; cycloalkylalkyl groups include cyclopentylmethyl group and cyclohexylmethyl group; cycloalkyl groups include cyclopropyl group, cyclobutyl group, cyclopentyl group, methylcyclopentyl group, cyclohexyl group, methylcyclohexyl group, cycloheptyl group and cyclooctyl group; and bicycloalkyl groups include norbornyl group, bicyclo[2.2.2]octyl group and adamantyl group.

The linear or branched alkenyl groups include vinyl group, allyl group, crotyl group (2-butenyl group) and isopropenyl group (1-methylvinyl group); cycloalkenyl or cycloalkadienyl groups include cyclopentenyl group, cyclopentadienyl group, cyclohexenyl group and cyclohexadienyl group.

The linear or branched alkynyl groups include ethynyl group, propynyl group and butynyl group. The aryl groups include phenyl group, 1-naphthyl group, 2-naphthyl group, 2-phenylphenyl group, 3-phenylphenyl group, 4-phenylphenyl group, 9-anthryl group, methylphenyl group, dimethylphenyl group, trimethylphenyl group, ethylphenyl group, methylethylphenyl group, diethylphenyl group, propylphenyl group and butylphenyl group.

The aralkyl group include benzyl group, 1-naphthylmethyl group, 2-naphthylmethyl group, phenethyl group (2-phenylethyl group), 1-phenylethyl group, phenylpropyl group, phenylbutyl group, phenylpentyl group, phenylhexyl group, methylbenzyl group, methylphenethyl group, dimethylbenzyl group, dimethylphenethyl group, trimethylbenzyl group, ethylbenzyl group and diethylbenzyl group.

The arylalkenyl groups include styryl group, methylstyryl group, ethylstyryl group, dimethylstyryl group and 3-phenyl-2-propenyl group.

The hydrocarbon groups of R$^2$ in which the CH$_2$ group is replaced with a carbonyl group, a sulfonyl group, O or S, or the C—H group is replaced with N, a C-halogen group or a C—CN group include groups having one or more structures such as ketone, aldehyde, carboxylic acid, ester, thioester, amide, carbonate, carbamate, sulfone, sulfonamide, ether, thioether, amine, alcohol, thiol, halogen and heterocycles (e.g. oxygen-containing heterocycle, sulfur-containing heterocycle, nitrogen-containing heterocycle). The oxygen-containing heterocycle, sulfur-containing heterocycle and nitrogen-containing heterocycle correspond to cyclic hydrocarbon groups in which their ring carbon is replaced with oxygen, sulfur and nitrogen, respectively. These heterocycles may contain two or more heteroatoms.

These substituted hydrocarbon groups may include a ketone structure such as acetylmethyl group; a sulfone structure such as methanesulfonylmethyl group; an ether structure such as methoxymethyl group, methoxyethyl group, ethoxyethyl group, methoxypropyl group, butoxyethyl group and ethoxyethoxyethyl group; a thioether structure such as methylthiomethyl group; an amine structure such as N-methylaminomethyl group, N,N-dimethylaminomethyl group, N-methylaminoethyl group, N-propylaminomethyl group and N-cyclopentylaminomethyl group; an ester structure such as methoxycarbonylmethyl group and acetoxymethyl group; an amide structure such as acetamidomethyl group and acetamidoethyl group; an oxygen-containing heterocycle such as tetrahydrofuranyl group, tetrahydropyranyl group and morphorylethyl group; an ether structure such as methoxyphenyl group; thioether structure such as methylthiophenyl group; a ketone structure such as acetylphenyl group; a carbonate structure such as methoxycarbonyloxyphenyl group, ethoxycarbonyloxyphenyl group and dimethoxyphenyl group; an ester structure such as methoxycarbonylphenyl group, acetoxyphenyl group and N-methylaminocarbonylphenyl group; an oxygen-containing aromatic ring such as furfuryl group; a sulfur-containing heterocycle such as thienyl group; a nitrogen-containing aromatic ring such as pyrrolyl group, benzofurfuryl group, imidazoyl group, oxazoyl group, thiadiazoyl group, pyridyl group, pyrimidyl group, pyridazinyl group, pyrazinyl group, tetrazinyl group, quinolyl group, isoquinolyl group, pyridylmethyl group, phenoxymethyl group and benzoyloxymethyl group; an alcohol structure such as 2-hydroxyethyl group; a thiol structure such as 2-mercaptoethyl group; an amine structure such as 2-aminoethyl group; 2-chloroethyl group, 2-hydroxypropyl group, 3-hydroxypropyl group, 2-mercaptopropyl group, 3-mercaptopropyl group, 2-aminopropyl group, 3-aminopropyl group, 2-chloropropyl group, 3-chloropropyl group, 2,3-dihydroxypropyl group, 2,3-dimercaptopropyl group, 2,3-diaminopropyl group, 2-amino-3-hydroxypropyl group, 3-amino-2-hydroxypropyl group, 2-hydroxybutyl group, 3-hydroxybutyl group, 4-hydroxybutyl group, 2-aminobutyl group, 3-aminobutyl group, 4-aminobutyl group, 2-mercaptobutyl group, 3-mercaptobutyl group, 4-mercaptobutyl group, 2-chlorobutyl group, 3-chlorobutyl group, 4-chlorobutyl group, 2,3-dihydroxybutyl group, 2,4-dihydroxybutyl group, 3,4-dihydroxybutyl group, 2,3-diaminobutyl group, 2,4-diaminobutyl group, 3,4-aminobutyl group, 2-amino-3-hydroxybutyl group, 3-amino-2-hydroxybutyl group, 2-amino-4-hydroxybutyl group, 4-amino-2-hydroxybutyl group, 3-amino-4-hydroxybutyl group, 4-amino-3-hydroxybutyl group, 2,3,4-trihydroxybutyl group, 2,3,4-triaminobutyl group, 2,4-diamino-3-hydroxybutyl group, 3-amino-2,4-dihydroxybutyl group, 2,3-diamino-4-hydroxybutyl group, 4-amino-2,3-dihydroxybutyl group, 3,4-diamino-2-hydroxybutyl group, 2-amino-3,4-dihydroxybutyl group, aminosulfonylphenyl group, hydroxyphenyl group, aminophenyl group, mercaptophenyl group, fluorophenyl group, chlorophenyl group, bromophenyl group, cyanophenyl group, dihydroxyphenyl group, diaminophenyl group, difluorophenyl group, dichlorophenyl group, dibromophenyl group, chlorofluorophenyl group, trifluorophenyl group, trichlorophenyl group, fluoromethylphenyl group, trifluoromethylphenyl group, aminomethylphenyl group, hydroxymethylphenyl group, hydroxyethylphenyl group, aminohydroxyphenyl group, fluorohydroxyphenyl group, chlorohydroxyphenyl group, hydroxycarbonylphenyl group and aminocarbonylphenyl group.

Preferred $R^2$ in the general formula (I) includes, as well as hydrogen, non-substituted or substituted hydrocarbon groups such as a linear or branched alkyl group, a linear or branched alkenyl group, a linear or branched alkadienyl group, particularly lower alkyl groups, in detail methyl group, ethyl group, propyl group, isopropyl, butyl group, pentyl group; or a cycloalkyl group, a cycloalkylalkyl group, an aryl group, an aralkyl group, particularly non-substituted or substituted benzyl group. Aromatic C—H(s) in the benzyl group may be replaced with a nitrogen atom, and hydrogen atoms on the phenyl ring may be replaced with amino groups or methyl groups as side chains. That is, the preferred $R^2$ also includes substituted benzyl groups such as 2-aminobenzyl group, 3-aminobenzyl group, 4-aminobenzyl group, or aza-substituted benzyl groups in which an aromatic C—H in their non-substituted or substituted benzyl group is replaced with a nitrogen atom such as 2-pyridylmethyl group, 3-pyridylmethyl group and 4-pyridylmethyl group, or these groups having said chains such as methyl group or substituted with amino groups or the like.

The hydrocarbon group of $R^9$ containing at most 14 carbon atoms includes a linear or branched chain hydrocarbon group, a monocyclic hydrocarbon group with or without side chain, a polycyclic hydrocarbon group with or without side chain, a spiro hydrocarbon group with or without side chain, a ring-assembling structural hydrocarbon group with or without side chain, or a chain hydrocarbon group substituted with said cylclic hydrocarbon groups. It includes any saturated or unsaturated hydrocarbon group, provided that unsaturated hydrocarbon groups having allene structure (C=C=C) are excluded. The linear or branched chain hydrocarbon group includes, for example, saturated chain hydrocarbon groups such as a linear alkyl group containing at least one carbon atom and a branched alkyl group containing at least three carbon atoms; unsaturated chain hydrocarbon groups such as a linear alkenyl group containing at least two carbon atoms, a branched alkenyl group containing at least three carbon atoms, a linear alkynyl group containing at least three carbon atoms, a branched alkynyl group containing at least four carbon atoms, a linear alkadienyl group containing at least four carbon atoms and a branched alkadienyl group containing at least five carbon atoms. The monocyclic hydrocarbon group includes, for example, saturated monocyclic hydrocarbon groups such as a cycloalkyl group without side chain which contains at least three carbon atoms and a cycloalkyl group with side chain which contains at least four carbon atoms in total; unsaturated monocyclic hydrocarbon groups such as a cycloalkenyl group without side chain which contains at least four carbon atoms, a cycloalkynyl group with side chain which contains at least five carbon atoms in total, a cycloalkadienyl group without side chain which contains at least five carbon atoms and a cycloalkadienyl group with side chain which contains at least six carbon atoms in total. The aromatic hydrocarbon group includes an aromatic group without side chain which contains 6 to 14 carbon atoms in total such as phenyl group, 1-naphthyl group, 2-naphthyl group and 9-anthryl group; an aromatic group with side chain which contains at least seven carbon atoms in total; phenylphenyl group containing 12 carbon atoms and phenylphenyl group with side chain which contains at least 13 carbon atoms in total which phenylphenyl groups are also included in a ring-assembling structural hydrocarbon group. The polycyclic hydrocarbon group includes a condensed cyclic hydrocarbon group without side chain which contains at least six carbon atoms, a condensed cyclic hydrocarbon group with side chain which contains at least seven carbon atoms in total, a bridged cyclic hydrocarbon group without side chain which contains at least seven carbon atoms in total, a bridged cyclic hydrocarbon group with side chain which contains at least eight carbon atoms in total, a spiro hydrocarbon group without side chain which contains at least nine carbon atoms in total and a spiro hydrocarbon group with side chain which contains at least 10 carbon atoms in total. In addition, said condensed cyclic hydrocarbon group without side chain includes those which contain at least nine carbon atoms in total when one of its condensed rings is benzene ring, and said condensed cyclic hydrocarbon group with side chain includes those which contain at least 10 carbon atoms in total when one of its condensed rings is benzene ring. The ring-assembling structural hydrocarbon group includes a cycloalkyl-cycloalkyl group without side chain which contains at least six carbon atoms in total, a cycloalkyl-cycloalkyl group with side chain which contains at least seven carbon atoms in total, a cycloalkylidene-cycloalkyl group without side chain which contains at least six carbon atoms in total and a cycloalkylidene-cycloalkyl group with side chain which contains at least seven carbon atoms in total. "A cyclic hydrocarbon with side chain" corresponds to one substituted with chain hydrocarbon group or groups on its ring. The chain hydrocarbon group substituted with said cyclic hydrocarbon groups includes a linear alkyl group which is substituted with an aromatic group without side chain and contains at least seven carbon atoms in total, a linear alkyl group which is substituted with an aromatic group with side chain and contains at least eight carbon atoms in total, a branched alkyl group which is substituted with an aromatic group without side chain and contains at least nine carbon atoms in total, a branched alkyl group which is substituted with an aromatic group with side chain and contains at least 10 carbon atoms in total, a linear alkenyl group which is substituted with an aromatic group without side chain and contains at least eight carbon atoms in total, a linear alkenyl group which is substituted with an aromatic group with side chain and contains at least nine carbon atoms in total, a branched alkenyl group which is substituted with an aromatic group without side chain and contains at least nine carbon atoms in total, a branched alkenyl group which is substituted with an aromatic group with side chain and contains at least 10 carbon atoms in total, a linear alkynyl group which is substituted with an aromatic group without side chain and contains at least eight carbon atoms in total, a linear alkynyl group which is substituted with an aromatic group with side chain and contains at least nine carbon atoms in total, a branched alkynyl group which is substituted with an aromatic group without side chain and contains at least 10 carbon atoms in total, a branched alkynyl group which is substituted with an aromatic group with side chain and contains at least 11 carbon atoms in total, a linear alkadienyl group which is substituted with an aromatic group without side chain and contains at least 10 carbon atoms in total, a linear alkadienyl group which is substituted with an aromatic group with side chain and contains at least 11 carbon atoms in total, a branched alkadienyl group which is substituted with an aromatic group without side chain and contains at least 11 carbon atoms in total, a branched alkadienyl group which is substituted with an aromatic group with side chain and contains at least 12 carbon atoms in total, a linear alkyl group which is substituted with a cycloalkyl group without side chain and contains at least four carbon atoms in total, a linear alkyl group which is substituted with a cycloalkyl group with side chain and contains at least five carbon atoms in total, a branched alkyl group which is substituted with a cycloalkyl group without side chain and contains at least six carbon atoms in total, a branched alkyl group which is substituted with a cycloalkyl group with side chain and contains at least seven carbon atoms in total, a linear alkenyl group which is substituted with a cycloalkyl group without side chain and contains at least five carbon atoms in total, a linear alkenyl group which is substituted with a cycloalkyl group with side chain and contains at least six carbon atoms in total, a branched alkenyl group which is substituted with a cycloalkyl group without side chain and contains at least six carbon atoms in total, a branched alkenyl group which is substituted with a cycloalkyl group with side chain and contains at least seven carbon atoms in total, a linear alkynyl group which is substituted with a cycloalkyl group without side chain and contains at least five carbon atoms in total, a linear alkynyl group which is substituted with a cycloalkyl group with side chain and contains at least six carbon atoms in total, a branched alkynyl group which is substituted with a cycloalkyl group without side chain and contains at least seven carbon atoms in total, a branched alkynyl group which is substituted with a cycloalkyl group with side chain and contains at least eight carbon atoms in total, a branched alkadienyl group which is substituted with a cycloalkyl group without side chain and contains at least eight carbon atoms in total, a branched alkadienyl group which is substituted with a cycloalkyl group with side chain and contains at least nine carbon atoms in total.

When $R^9$ is an aromatic group without side chain, an aromatic group with side chain, phenylphenyl group or phenylphenyl group with side chain, it refers to an aryl group, and a linear or branched alkyl group substituted with the aryl group or groups refers to an aralkyl group. Other cyclic hydrocarbon groups including both of one having side chains on their ring and one having no side chain simply refer to, for example, cycloalkyl groups, unless otherwise mentioned. Further, chain hydrocarbon groups including both of linear one and branched one simply refer to, for example, alkyl groups.

When —CH$_2$— in said hydrocarbon group is replaced with a carbonyl group, sulfonyl group, —O— or —S—, ketone, sulfon, ether or thioether structure is introduced thereinto, respectively. When —CH$_2$— in —CH$_3$ is replaced with a carbonyl group, —O— or —S—, it converts into formyl (aldehyde) group, hydroxyl group or mercapto group, respectively. When a terminal =CH$_2$ is replaced with =O or =S, ketone or thioketone is introduced thereinto. When C—H in —CH$_2$— is replaced with N, it converts into —NH—. When C—H in >CH— is replaced with N, it converts into >N—. When C—H in =CH— is replaced with N, it converts into =N—. When C—H in a terminal —CH$_3$ is replaced with N, —NH$_2$ is introduced thereinto. When C—H in =CH$_2$ is replaced with N, it converts into =NH. When C—H in C≡CH is replaced with N, it converts into cyano group (C≡N). Further, C—H in —CH$_3$, —CH$_2$—, =CH—, ≡CH or >CH— is replaced with a C-halogen group or a C—CN group, said carbon is substituted with halogeno group or cyano group. The replacement of carbon chains with —O—, —S— or N corresponds to oxa-, thia- or aza-substitution of said hydrocarbon group, respectively. For example, when these substitution take place in a ring carbon of the hydrocarbon ring, the hydrocarbon ring converts into a heterocyclic ring respectively containing oxygen, sulfur or nitrogen. The replacement of CH$_2$ and C—H in said hydrocarbon group may independently take place and it may further take place when CH$_2$ or C—H still remains on said carbon after the prior replacement. Further, these replacements may bring conversions such as conversion of —CH$_2$—CH$_2$— into —CO—O— (ester structure) and —CO—S— (thioester structure); conversion of —CH$_2$—CH$_2$—CH$_2$— into —O—CO—O— (carbonate structure) and —NH—CO—NH (urea ester structure); and conversion of —CH$_2$—CH$_3$ into —CO—O—H (carboxylic acid structure), —CO—NH$_2$ (amide structure) and —SO$_2$—NH$_2$ (sulfonamide structure). The halogen includes fluorine, chlorine, bromine and iodine, particularly fluorine, chlorine and bromine being preferred.

Accordingly, the hydrocarbon group of $R^9$ containing at most 14 carbon atoms may be selected from any chain hydrocarbon group and ring-structural hydrocarbon group such as cyclic hydrocarbon groups, for example, saturated chain hydrocarbon groups such as linear or branched alkyl groups; unsaturated chain hydrocarbon groups such as linear or branched alkenyl groups, linear or branched alkynyl groups and linear or branched alkadienyl groups; saturated cyclic hydrocarbon groups such as cycloalkyl groups; unsaturated cyclic hydrocarbon groups such as cycloalkenyl groups, cycloalkynyl groups and cycloalkadienyl groups; and aromatic hydrocarbon groups such as aryl groups, aralkyl groups and arylalkenyl groups.

In more detail, the linear or branched alkyl groups include methyl group, ethyl group, propyl group, isopropyl group, butyl group, 1-methylpropyl group, pentyl group, 1-methylbutyl group, hexyl group, 1-methylpentyl group, heptyl group, 1-methylhexyl group, 1-ethylpentyl group, octyl group, nonyl group, decyl group, undecyl group, dodecyl group, tridecyl group, tetradecyl group, 2-methylpropyl group, 2-methylbutyl group, 3-methylbutyl group, 2-methylpentyl group, 3-methylpentyl group, 4-methylpentyl group, methylhexyl group, methylheptyl group, methyloctyl group, methylnonyl group, 1,1-dimethylethyl group, 1,1-dimethylpropyl group, 2,6-dimethylheptyl group, 3,7-dimethyloctyl group and 2-ethylhexyl group; cycloalkylalkyl groups include cyclopentylmethyl group and cyclohexylmethyl group; cycloalkyl groups include cyclopropyl group, cyclobutyl group, cyclopentyl group, methylcyclopentyl group, cyclohexyl group, methylcyclohexyl group, cycloheptyl group and cyclooctyl group; and bicycloalkyl groups include norbornyl group, bicyclo[2.2.2]octyl group and adamantyl group.

The linear or branched alkenyl groups include vinyl group, allyl group, crotyl group (2-butenyl group) and isopropenyl group (1-methylvinyl group); cycloalkenyl or cycloalkadienyl groups include cyclopentenyl group, cyclopentadienyl group, cyclohexenyl group and cyclohexadienyl group.

The linear or branched alkynyl groups include ethynyl group, propynyl group and butynyl group. The aryl groups include phenyl group, 1-naphthyl group, 2-naphthyl group, 2-phenylphenyl group, 3-phenylphenyl group, 4-phenylphenyl group, 9-anthryl group, methylphenyl group, dimethylphenyl group, trimethylphenyl group, ethylphenyl group, methylethylphenyl group, diethylphenyl group, propylphenyl group and butylphenyl group.

The aralkyl group include benzyl group, 1-naphthylmethyl group, 2-naphthylmethyl group, phenethyl group (2-phenylethyl group), 1-phenylethyl group, phenylpropyl group, phenylbutyl group, phenylpentyl group, phenylhexyl group, methylbenzyl group, methylphenethyl group, dimethylbenzyl group, dimethylphenethyl group, trimethylbenzyl group, ethylbenzyl group and diethylbenzyl group.

The arylalkenyl groups include styryl group, methylstyryl group, ethylstyryl group, dimethylstyryl group and 3-phenyl-2-propenyl group.

The hydrocarbon groups of $R^9$ in which the $CH_2$ group is replaced with a carbonyl group, a sulfonyl group, O or S, or the C—H group is replaced with N, a C-halogen group or a C—CN group include groups having one or more structures such as ketone, aldehyde, carboxylic acid, ester, thioester, amide, carbonate, carbamate, sulfone, sulfonamide, ether, thioether, amine, alcohol, thiol, halogen and heterocycles (e.g. oxygen-containing heterocycle, sulfur-containing heterocycle, nitrogen-containing heterocycle). The oxygen-containing heterocycle, sulfur-containing heterocycle and nitrogen-containing heterocycle correspond to cyclic hydrocarbon groups in which their ring carbon is replaced with oxygen, sulfur and nitrogen, respectively. These heterocycles may contain two or more heteroatoms.

These substituted hydrocarbon groups may include a ketone structure such as acetylmethyl group; a sulfone structure such as methanesulfonylmethyl group; an ether structure such as methoxymethyl group, methoxyethyl group, ethoxyethyl group, methoxypropyl group, butoxyethyl group and ethoxyethoxyethyl group; a thioether structure such as methylthiomethyl group; an amine structure such as N-methylaminomethyl group, N,N-dimethylaminomethyl group, N-methylaminoethyl group, N-propylaminomethyl group and N-cyclopentylaminomethyl group; an ester structure such as methoxycarbonylmethyl group and acetoxymethyl group; an amide structure such as acetamidomethyl group and acetamidoethyl group; an oxygen-containing heterocycle such as tetrahydrofuranyl group, tetrahydropyranyl group and morphorylethyl group; an ether structure such as methoxyphenyl group; thioether structure such as methylthiophenyl group; a ketone structure such as acetylphenyl group; a carbonate structure such as methoxycarbonyloxyphenyl group, ethoxycarbonyloxyphenyl group and dimethoxyphenyl group; an ester structure such as methoxycarbonylphenyl group, acetoxyphenyl group and N-methylaminocarbonylphenyl group; an oxygen-containing aromatic ring such as furfuryl group; a sulfur-containing heterocycle such as thienyl group; a nitrogen-containing aromatic ring such as pyrrolyl group, benzofurfuryl group, imidazoyl group, oxazoyl group, thiadiazoyl group, pyridyl group, pyrimidyl group, pyridazinyl group, pyrazinyl group, tetrazinyl group, quinolyl group, isoquinolyl group, pyridylmethyl group, phenoxymethyl group and benzoyloxymethyl group; an alcohol structure such as 2-hydroxyethyl group; a thiol structure such as 2-mercaptoethyl group; an amine structure such as 2-aminoethyl group; 2-chloroethyl group, 2-hydroxypropyl group, 3-hydroxypropyl group, 2-mercaptopropyl group, 3-mercaptopropyl group, 2-aminopropyl group, 3-aminopropyl group, 2-chloropropyl group, 3-chloropropyl group, 2,3-dihydroxypropyl group, 2,3-dimercaptopropyl group, 2,3-diaminopropyl group, 2-amino-3-hydroxypropyl group, 3-amino-2-hydroxypropyl group, 2-hydroxybutyl group, 3-hydroxybutyl group, 4-hydroxybutyl group, 2-aminobutyl group, 3-aminobutyl group, 4-aminobutyl group, 2-mercaptobutyl group, 3-mercaptobutyl group, 4-mercaptobutyl group, 2-chlorobutyl group, 3-chlorobutyl group, 4-chlorobutyl group, 2,3-dihydroxybutyl group, 2,4-dihydroxybutyl group, 3,4-dihydroxybutyl group, 2,3-diaminobutyl group, 2,4-diaminobutyl group, 3,4-aminobutyl group, 2-amino-3-hydroxybutyl group, 3-amino-2-hydroxybutyl group, 2-amino-4-hydroxybutyl group, 4-amino-2-hydroxybutyl group, 3-amino-4-hydroxybutyl group, 4-amino-3-hydroxybutyl group, 2,3,4-trihydroxybutyl group, 2,3,4-triaminobutyl group, 2,4-diamino-3-hydroxybutyl group, 3-amino-2,4-dihydroxybutyl group, 2,3-diamino-4-hydroxybutyl group, 4-amino-2,3-dihydroxybutyl group, 3,4-diamino-2-hydroxybutyl group, 2-amino-3,4-dihydroxybutyl group, aminosulfonylphenyl group, hydroxyphenyl group, aminophenyl group, mercaptophenyl group, fluorophenyl group, chlorophenyl group, bromophenyl group, cyanophenyl group, dihydroxyphenyl group, diaminophenyl group, difluorophenyl group, dichlorophenyl group, dibromophenyl group, chlorofluorophenyl group, trifluorophenyl group, trichlorophenyl group, fluoromethylphenyl group, trifluoromethylphenyl group, aminomethylphenyl group, hydroxymethylphenyl group, hydroxyethylphenyl group, aminohydroxyphenyl group, fluorohydroxyphenyl group, chlorohydroxyphenyl group, hydroxycarbonylphenyl group and aminocarbonylphenyl group.

Preferred $R^9$ in the general formula (I) includes non-substituted or substituted hydrocarbon groups such as an alkyl group, particularly lower alkyl groups, an alkenyl group, an alkadienyl group, a cycloalkyl group, an aryl group, and an aralkyl group, particularly benzyl group and substituted benzyl group. Aromatic C—H(s) in the benzyl group may be replaced with a nitrogen atom and hydrogen atoms on the phenyl ring may be replaced with halogeno groups, particularly chloro, bromo, fluoro, trifluoromethyl or amino groups, or substituted with lower alkyl groups such as methyl group as side chains. In addition, the preferred $R^9$ also includes alkyl groups substituted with oxygen-containing heterocycles, sulfur-containing heterocycles and nitrogen-containing heterocycles, which heterocycles are similar to an aralkyl group and have aromaticity and may further have substituents or side chains. In more detail, the preferred substituted benzyl group includes 2-chlorobenzyl group, 3-chlorobenzyl group, 4-chlorobenzyl group, 2-bromobenzyl group, 3-bromobenzyl group, 4-bromobenzyl group, 2-trifluoromethylbenzyl group, 3-trifluoromethylbenzyl group, 4-trifluoromethylbenzyl group, 2-aminobenzyl group, 3-aminobenzyl group, 4-aminobenzyl group, 2,3-dichlorobenzyl group, 3,4-dichlorobenzyl group, 3,5-dichlorobenzyl group, 4-amino-3-chlorobenzyl group, 3-amino-4-chlorobenzyl group, 4-amino-3-bromobenzyl group, 3-amino-4-bromobenzyl group, aza-substituted groups in which C—H in benzene ring of non-substituted or substituted benzyl groups is replaced with a nitrogen atom, for example, 2-pyridylmethyl group, 3-pyridylmethyl group and 4-pyridylmethyl group. In the alkyl groups substituted with oxygen-containing heterocycles, sulfur-containing heterocycles or nitrogen-containing heterocycles, which heterocycles have aromaticity and may further have substituents, the oxygen-containing heterocycles, sulfur-containing heterocycles and nitrogen-containing heterocycles having aromaticity include monoheteroatom-substituted five-membered ring such as furan ring, thiophene ring and pyrrole ring; diheteroatom-substituted five-membered ring such as oxazole ring, thiazole ring, imidazole ring, isoxazole ring, isothiazole ring and pyrazole ring; monoaza-substituted six-membered benzene ring such as pyrimidine ring; diaza-substituted benzene ring such as pyrimidine ring, pyrazine ring and pyridazine ring; triaza-substituted benzene ring such as triazine ring; bicyclic compounds thereof condensed with said five-membered ring or benzene ring or aza-substituted benzene ring, for example, condensed substituents of the five-membered ring and six-membered ring such as benzofuran ring, benzothiophene ring, benzopyrrole ring and benzimidazole ring, condensed substituents of the six-membered rings, which correspond to aza-substituted naphthalene ring (azanaphthalene ring), such as quinoline ring, isoquinoline ring and quinoxaline ring; 4H-pyran-4-one structure forming an aromatic ring-like conjugated system with oxo group substituted onto its ring; or any structure forming an aromatic ring-like conjugated system as a whole such as 1,4-dithianaphthalene ring. Among these alkyl groups substituted with said oxygen-containing heterocycles, sulfur-containing heterocycles or nitrogen-containing heterocycles having aromaticity, more preferred are the structures similar to non-substituted or substituted benzyl group, i.e., methyl group substituted with said oxygen-containing heterocycles, sulfur-containing heterocycles or nitrogen-containing heterocycles, particularly monocyclic heterocycles, as well as non-substituted or substituted benzyl group. In addition, the substituted benzyl groups may have suitable substituents or side chains on their ring.

The hydrocarbon group in the amino group of $R^6$ which is mono-substituted or di-substituted with a hydrocarbon group containing at most 10 carbon atoms includes a linear or branched chain hydrocarbon group, a monocyclic hydrocarbon group with or without side chain, a polycyclic hydrocarbon group with or without side chain, a spiro hydrocarbon group with or without side chain, a ring-assembling structural hydrocarbon group with or without side chain, or a chain hydrocarbon group substituted with said cylclic hydrocarbon groups. It includes any saturated or unsaturated hydrocarbon group, provided that unsaturated hydrocarbon groups having allene structure (C=C=C) are excluded. The linear or branched chain hydrocarbon group includes, for example, saturated chain hydrocarbon groups such as a linear alkyl group containing at least one carbon atom and a branched alkyl group containing at least three carbon atoms; unsaturated chain hydrocarbon groups such as a linear alkenyl group containing at least two carbon atoms, a branched alkenyl group containing at least three carbon atoms, a linear alkynyl group containing at least three carbon atoms, a branched alkynyl group containing at least four carbon atoms, a linear alkadienyl group containing at least four carbon atoms and a branched alkadienyl group containing at least five carbon atoms. The monocyclic hydrocarbon group includes, for example, saturated monocyclic hydrocarbon groups such as a cycloalkyl group without side chain which contains at least three carbon atoms and a cycloalkyl group with side chain which contains at least four carbon atoms in total; unsaturated monocyclic hydrocarbon groups such as a cycloalkenyl group without side chain which contains at least four carbon atoms, a cycloalkynyl group with side chain which contains at least five carbon atoms in total, a cycloalkadienyl group without side chain which contains at least five carbon atoms and a cycloalkadienyl group with side chain which contains at least six carbon atoms in total. The aromatic hydrocarbon group includes an aromatic group without side chain which contains 6 to 10 carbon atoms in total such as phenyl group, 1-naphthyl group and 2-naphthyl group; and an aromatic group with side chain which contains at least seven carbon atoms in total. The polycyclic hydrocarbon group includes a condensed cyclic hydrocarbon group without side chain which contains at least six carbon atoms, a condensed cyclic hydrocarbon group with side chain which contains at least seven carbon atoms in total, a bridged cyclic hydrocarbon group without side chain which contains at least seven carbon atoms, a bridged cyclic hydrocarbon group with side chain which contains at least eight carbon atoms in total and a spiro hydrocarbon group without side chain which contains at least nine carbon atoms in total. In addition, said condensed cyclic hydrocarbon group without side chain includes those which contain at least nine carbon atoms in total when one of its condensed rings is benzene ring, and said condensed cyclic hydrocarbon group with side chain includes those which contain 10 carbon atoms in total when one of its condensed rings is benzene ring. The ring-assembling structural hydrocarbon group includes a cycloalkyl-cycloalkyl group without side chain which contains at least six carbon atoms in total, a cycloalkyl-cycloalkyl group with side chain which contains at least seven carbon atoms in total, a cycloalkylidene-cycloalkyl group without side chain which contains at least six carbon atoms in total and a cycloalkylidene-cycloalkyl group with side chain which contains at least seven carbon atoms in total. "A cyclic hydrocarbon with side chain" corresponds to one substituted with chain hydrocarbon group or groups on its ring. The chain hydrocarbon group substituted with said cyclic hydrocarbon groups includes a linear alkyl group which is substituted with an aromatic group without side chain and contains at least seven carbon atoms in total, a linear alkyl group which is substituted with an aromatic group with side chain and contains at least eight carbon atoms in total, a branched alkyl group which is substituted with an aromatic group without side chain and contains at least nine carbon atoms in total, a branched alkyl group which is substituted with an aromatic group with side chain and contains 10 carbon atoms in total, a linear alkenyl group which is substituted with an aromatic group without side chain and contains at least eight carbon atoms in total, a linear alkenyl group which is substituted with an aromatic group with side chain and contains at least nine carbon atoms in total, a branched alkenyl group which is substituted with an aromatic group without side chain and contains at least nine carbon atoms in total, a branched alkenyl group which is substituted with an aromatic group with side chain and contains 10 carbon atoms in total, a linear alkynyl group which is substituted with an aromatic group without side chain and contains at least eight carbon atoms in total, a linear alkynyl group which is substituted with an aromatic group with side chain and contains at least nine carbon atoms in total, a branched alkynyl group which is substituted with an aromatic group without side chain and contains 10 carbon atoms in total, a linear alkadienyl group which is substituted with an aromatic group without side chain and contains 10 carbon atoms in total, a linear alkyl group which is substituted with a cycloalkyl group without side chain and contains at least four carbon atoms in total, a linear alkyl group which is substituted with a cycloalkyl group with side chain and contains at least five carbon atoms in total, a branched alkyl group which is substituted with a cycloalkyl group without side chain and contains at least six carbon atoms in total, a branched alkyl group which is substituted with a cycloalkyl group with side chain and contains at least seven carbon atoms in total, a linear alkenyl group which is substituted with a cycloalkyl group without side chain and contains at least five carbon atoms in total, a linear alkenyl group which is substituted with a cycloalkyl group with side chain and contains at least six carbon atoms in total, a branched alkenyl group which is substituted with a cycloalkyl group without side chain and contains at least six carbon atoms in total, a branched alkenyl group which is substituted with a cycloalkyl group with side chain and contains at least seven carbon atoms in total, a linear alkynyl group which is substituted with a cycloalkyl group without side chain and contains at least five carbon atoms in total, a linear alkynyl group which is substituted with a cycloalkyl group with side chain and contains at least six carbon atoms in total, a branched alkynyl group which is substituted with a cycloalkyl group without side chain and contains at least seven carbon atoms in total, a branched alkynyl group which is substituted with a cycloalkyl group with side chain and contains at least eight carbon atoms in total, a branched alkadienyl group which is substituted with a cycloalkyl group without side chain and contains at least eight carbon atoms in total, a branched alkadienyl group which is substituted with a cycloalkyl group with side chain and contains at least nine carbon atoms in total.

When a hydrocarbon group in the mono- or di-substituted amino group of $R^6$ is an aromatic group without side chain or an aromatic group with side chain, it refers to an aryl group, and a linear or branched alkyl group substituted with the aryl group or groups refers to an aralkyl group. Other cyclic hydrocarbon groups including both of one having side chains on their ring and one having no side chain simply refer to, for example, cycloalkyl groups, unless otherwise mentioned. Further, chain hydrocarbon groups including both of linear one and branched one simply refer to, for example, alkyl groups.

Accordingly, the hydrocarbon group in the amino group of $R^6$ which is mono-substituted or di-substituted with a hydrocarbon group containing at most 10 carbon atoms may be selected from any chain hydrocarbon group and ring-structural hydrocarbon group such as cyclic hydrocarbon groups, for example, saturated chain hydrocarbon groups such as linear or branched alkyl groups; unsaturated chain hydrocarbon groups such as linear or branched alkenyl groups, linear or branched alkynyl groups and linear or branched alkadienyl groups; saturated cyclic hydrocarbon groups such as cycloalkyl groups; unsaturated cyclic hydrocarbon groups such as cycloalkenyl groups, cycloalkynyl groups and cycloalkadienyl groups; and aromatic hydrocarbon groups such as aryl groups, aralkyl groups and arylalkenyl groups.

In more detail, the linear or branched alkyl groups include methyl group, ethyl group, propyl group, isopropyl group, butyl group, 1-methylpropyl group, pentyl group, 1-methylbutyl group, hexyl group, 1-methylpentyl group, heptyl group, 1-methylhexyl group, 1-ethylpentyl group, octyl group, nonyl group, decyl group, 2-methylpropyl group, 2-methylbutyl group, 3-methylbutyl group, 2-methylpentyl group, 3-methylpentyl group, 4-methylpentyl group, methylhexyl group, methylheptyl group, methyloctyl group, methylnonyl group, 1,1-dimethylethyl group, 1,1-dimethylpropyl group, 2,6-dimethylheptyl group, 3,7-dimethyloctyl group and 2-ethylhexyl group; cycloalkylalkyl groups include cyclopentylmethyl group and cyclohexylmethyl group; cycloalkyl groups include cyclopropyl group, cyclobutyl group, cyclopentyl group, methylcyclopentyl group, cyclohexyl group, methylcyclohexyl group, cycloheptyl group and cyclooctyl group; and bicycloalkyl groups include norbornyl group, bicyclo[2.2.2]octyl group and adamantyl group.

The linear or branched alkenyl groups include vinyl group, allyl group, crotyl group (2-butenyl group) and isopropenyl group (1-methylvinyl group); cycloalkenyl or cycloalkadienyl groups include cyclopentenyl group, cyclopentadienyl group, cyclohexenyl group and cyclohexadienyl group.

The linear or branched alkynyl groups include ethynyl group, propynyl group and butynyl group. The aryl groups include phenyl group, 1-naphthyl group, 2-naphthyl group, methylphenyl group, dimethylphenyl group, trimethylphenyl group, ethylphenyl group, methylethylphenyl group, diethylphenyl group, propylphenyl group and butylphenyl group.

The aralkyl group include benzyl group, phenethyl group (2-phenylethyl group), 1-phenylethyl group, phenylpropyl group, phenylbutyl group, methylbenzyl group, methylphenethyl group, dimethylbenzyl group, dimethylphenethyl group, trimethylbenzyl group and ethylbenzyl group.

The arylalkenyl groups include styryl group, methylstyryl group, ethylstyryl group, dimethylstyryl group and 3-phenyl-2-propenyl group.

The amino group of $R^6$ which is mono-substituted with a hydrocarbon group containing at most 10 carbon atoms includes methylamino group, ethylamino group, propylamino group, allylamino group, butylamino group, pentylamino group, cyclopropylamino group, cyclobutylamino group, cyclopentylamino group, cyclohexylamino group, norbornylamino group, bicyclo[2.2.2]octylamino group, phenylamino group, naphthylamino group, (methylphenyl) amino group, (dimethylphenyl)amino group, (ethylphenyl) amino group, benzylamino group, (methylbenzyl)amino group, (dimethylbenzyl)amino group, (ethylbenzyl)amino group, and phenethylamino group. The amino group which is di-substituted with a hydrocarbon group containing at most 10 carbon atoms includes dimethylamino group, diethylamino group, dipropylamino group, diallylamino group, dibutylamino group, N-methyl-N-propylamino group, diphenylamino group, bis(methylphenyl)amino group, dibenzylamino group, bis(methylbenzyl)amino group, N-phenyl-N-methylamino group and N-benzyl-N-methylamino group.

The acyloxy group of $R^8$ containing at most 18 carbon atoms in the general formula (I) means an oxy group substituted with an acyl group, which acyl group is obtained by substituting a carbonyl group with a hydrogen or a hydrocarbon group containing at most 17 carbon atoms.

The hydrocarbon group containing at most 17 carbon atoms in the acyloxy group of $R^8$ containing at most 18 carbon atoms includes a linear or branched chain hydrocarbon group, a monocyclic hydrocarbon group with or without side chain, a polycyclic hydrocarbon group with or without side chain, a Spiro hydrocarbon group with or without side chain, a ring-assembling structural hydrocarbon group with or without side chain, or a chain hydrocarbon group substituted with said cylclic hydrocarbon groups. It includes any saturated or unsaturated hydrocarbon group, provided that unsaturated hydrocarbon groups having allene structure (C=C=C) are excluded. The linear or branched chain hydrocarbon group includes, for example, saturated chain hydrocarbon groups such as a linear alkyl group containing at least one carbon atom and a branched alkyl group containing at least three carbon atoms; unsaturated chain hydrocarbon groups such as a linear alkenyl group containing at least two carbon atoms, a branched alkenyl group containing at least three carbon atoms, a linear alkynyl group containing at least three carbon atoms, a branched alkynyl group containing at least four carbon atoms, a linear alkadienyl group containing at least four carbon atoms and a branched alkadienyl group containing at least five carbon atoms. The monocyclic hydrocarbon group includes, for example, saturated monocyclic hydrocarbon groups such as a cycloalkyl group without side chain which contains at least three carbon atoms and a cycloalkyl group with side chain which contains at least four carbon atoms in total; unsaturated monocyclic hydrocarbon groups such as a cycloalkenyl group without side chain which contains at least four carbon atoms, a cycloalkynyl group with side chain which contains at least five carbon atoms in total, a cycloalkadienyl group without side chain which contains at least five carbon atoms and a cycloalkadienyl group with side chain which contains at least six carbon atoms in total. The aromatic hydrocarbon group includes an aromatic group without side chain which contains at least six carbon atoms in total such as phenyl group, 1-naphthyl group, 2-naphthyl group and 9-anthryl group; an aromatic group with side chain which contains at least seven carbon atoms in total; phenylphenyl group containing 12 carbon atoms and phenylphenyl group with side chain which contains at least 13 carbon atoms in total which phenylphenyl groups are also included in a ring-assembling structural hydrocarbon group. The polycyclic hydrocarbon group includes a condensed cyclic hydrocarbon group without side chain which contains at least six carbon atoms, a condensed cyclic hydrocarbon group with side chain which contains at least seven carbon atoms in total, a bridged cyclic hydrocarbon group without side chain which contains at least seven carbon atoms, a bridged cyclic hydrocarbon group with side chain which contains at least eight carbon atoms in total, a spiro hydrocarbon group without side chain which contains at least nine carbon atoms in total and a spiro hydrocarbon group with side chain which contains at least 10 carbon atoms in total. In addition, said condensed cyclic hydrocarbon group without side chain includes those which contain at least nine carbon atoms in total when one of its condensed rings is benzene ring, and said condensed cyclic hydrocarbon group with side chain includes those which contain at least 10 carbon atoms in total when one of its condensed rings is benzene ring. The ring-assembling structural hydrocarbon group includes a cycloalkyl-cycloalkyl group without side chain which contains at least six carbon atoms in total, a cycloalkyl-cycloalkyl group with side chain which contains at least seven carbon atoms in total, a cycloalkylidene-cycloalkyl group without side chain which contains at least six carbon atoms in total and a cycloalkylidene-cycloalkyl group with side chain which contains at least seven carbon atoms in total. "A cyclic hydrocarbon with side chain" corresponds to one substituted with chain hydrocarbon group or groups on its ring. The chain hydrocarbon group substituted with said cyclic hydrocarbon groups includes a linear alkyl group which is substituted with an aromatic group without side chain and contains at least seven carbon atoms in total, a linear alkyl group which is substituted with an aromatic group with side chain and contains at least eight carbon atoms in total, a branched alkyl group which is substituted with an aromatic group without side chain and contains at least nine carbon atoms in total, a branched alkyl group which is substituted with an aromatic group with side chain and contains at least 10 carbon atoms in total, a linear alkenyl group which is substituted with an aromatic group without side chain and contains at least eight carbon atoms in total, a linear alkenyl group which is substituted with an aromatic group with side chain and contains at least nine carbon atoms in total, a branched alkenyl group which is substituted with an aromatic group without side chain and contains at least nine carbon atoms in total, a branched alkenyl group which is substituted with an aromatic group with side chain and contains at least 10 carbon atoms in total, a linear alkynyl group which is substituted with an aromatic group without side chain and contains at least eight carbon atoms in total, a linear alkynyl group which is substituted with an aromatic group with side chain and contains at least nine carbon atoms in total, a branched alkynyl group which is substituted with an aromatic group without side chain and contains at least 10 carbon atoms in total, a branched alkynyl group which is substituted with an aromatic group with side chain and contains at least 11 carbon atoms in total, a linear alkadienyl group which is substituted with an aromatic group without side chain and contains at least 10 carbon atoms in total, a linear alkadienyl group which is substituted with an aromatic group with side chain and contains at least 11 carbon atoms in total, a branched alkadienyl group which is substituted with an aromatic group without side chain and contains at least 11 carbon atoms in total, a branched alkadienyl group which is substituted with an aromatic group with side chain and contains at least 12 carbon atoms in total, a linear alkyl group which is substituted with a cycloalkyl group without side chain and contains at least four carbon atoms in total, a linear alkyl group which is substituted with a cycloalkyl group with side chain and contains at least five carbon atoms in total, a branched alkyl group which is substituted with a cycloalkyl group without side chain and contains at least six carbon atoms in total, a branched alkyl group which is substituted with a cycloalkyl group with side chain and contains at least seven carbon atoms in total, a linear alkenyl group which is substituted with a cycloalkyl group without side chain and contains at least five carbon atoms in total, a linear alkenyl group which is substituted with a cycloalkyl group with side chain and contains at least six carbon atoms in total, a branched alkenyl group which is substituted with a cycloalkyl group without side chain and contains at least six carbon atoms in total, a branched alkenyl group which is substituted with a cycloalkyl group with side chain and contains at least seven carbon atoms in total, a linear alkynyl group which is substituted with a cycloalkyl group without side chain and contains at least five carbon atoms in total, a linear alkynyl group which is substituted with a cycloalkyl group with side chain and contains at least six carbon atoms in total, a branched alkynyl group which is substituted with a cycloalkyl group without side chain and contains at least seven carbon atoms in total, a branched alkynyl group which is substituted with a cycloalkyl group with side chain and contains at least eight carbon atoms in total, a branched alkadienyl group which is substituted with a cycloalkyl group without side chain and contains at least eight carbon atoms in total, a branched alkadienyl group which is substituted with a cycloalkyl group with side chain and contains at least nine carbon atoms in total.

When the hydrocarbon group in the acyloxy group of $R^8$ is an aromatic group without side chain, an aromatic group with side chain, phenylphenyl group or phenylphenyl group with side chain, it refers to an aryl group, and a linear or branched alkyl group substituted with the aryl group or groups refers to an aralkyl group. Other cyclic hydrocarbon groups including both of one having side chains on their ring and one having no side chain simply refer to, for example, cycloalkyl groups, unless otherwise mentioned. Further, chain hydrocarbon groups including both of linear one and branched one simply refer to, for example, alkyl groups.

Accordingly, the hydrocarbon group containing at most 17 carbon atoms in the acyloxy group of $R^8$ containing at most 18 carbon atoms may be selected from any chain hydrocarbon group and ring-structural hydrocarbon group such as cyclic hydrocarbon groups, for example, saturated chain hydrocarbon groups such as linear or branched alkyl groups; unsaturated chain hydrocarbon groups such as linear or branched alkenyl groups, linear or branched alkynyl groups and linear or branched alkadienyl groups; saturated cyclic hydrocarbon groups such as cycloalkyl groups; unsaturated cyclic hydrocarbon groups such as cycloalkenyl groups, cycloalkynyl groups and cycloalkadienyl groups; and aromatic hydrocarbon groups such as aryl groups, aralkyl groups and arylalkenyl groups.

In more detail, the linear or branched alkyl groups include methyl group, ethyl group, propyl group, isopropyl group, butyl group, 1-methylpropyl group, pentyl group, 1-methylbutyl group, hexyl group, 1-methylpentyl group, heptyl group, 1-methylhexyl group, 1-ethylpentyl group, octyl group, nonyl group, decyl group, undecyl group, dodecyl group, tridecyl group, tetradecyl group, 2-methylpropyl group, 2-methylbutyl group, 3-methylbutyl group, 2-methylpentyl group, 3-methylpentyl group, 4-methylpentyl group, methylhexyl group, methylheptyl group, methyloctyl group, methylnonyl group, 1,1-dimethylethyl group, 1,1-dimethylpropyl group, 2,6-dimethylheptyl group, 3,7-dimethyloctyl group and 2-ethylhexyl group; cycloalkylalkyl groups include cyclopentylmethyl group and cyclohexylmethyl group; cycloalkyl groups include cyclopropyl group, cyclobutyl group, cyclopentyl group, methylcyclopentyl group, cyclohexyl group, methylcyclohexyl group, cycloheptyl group and cyclooctyl group; and bicycloalkyl groups include norbornyl group, bicyclo[2.2.2]octyl group and adamantyl group.

The linear or branched alkenyl groups include vinyl group, allyl group, crotyl group (2-butenyl group) and isopropenyl group (1-methylvinyl group); cycloalkenyl or cycloalkadienyl groups include cyclopentenyl group, cyclopentadienyl group, cyclohexenyl group and cyclohexadienyl group.

The linear or branched alkynyl groups include ethynyl group, propynyl group and butynyl group. The aryl groups include phenyl group, 1-naphthyl group, 2-naphthyl group, 2-phenylphenyl group, 3-phenylphenyl group, 4-phenylphenyl group, 9-anthryl group, methylphenyl group, dimethylphenyl group, trimethylphenyl group, ethylphenyl group, methylethylphenyl group, diethylphenyl group, propylphenyl group and butylphenyl group.

The aralkyl group include benzyl group, 1-naphthylmethyl group, 2-naphthylmethyl group, phenethyl group (2-phenylethyl group), 1-phenylethyl group, phenylpropyl group, phenylbutyl group, phenylpentyl group, phenylhexyl group, methylbenzyl group, methylphenethyl group, dimethylbenzyl group, dimethylphenethyl group, trimethylbenzyl group, ethylbenzyl group and diethylbenzyl group.

The arylalkenyl groups include styryl group, methylstyryl group, ethylstyryl group, dimethylstyryl group and 3-phenyl-2-propenyl group.

The acyloxy group of $R^8$ containing at most 18 carbon atoms includes formyloxy group, acetyloxy group, propionyloxy group, butanoyloxy group, pentanoyloxy group, hexanoyloxy group, heptanoyloxy group, octanoyloxy group, nonanoyloxy group, decanoyloxy group, undecanoyloxy group, dodecanoyloxy group, tridecanoyloxy group, tetradecanoyloxy group, pentadecanoyl group, hexadecanoyloxy group, heptadecanoyloxy group, octadecanoyloxy group, 2,2-dimethylpropanoyloxy group, benzoyloxy group, methylbenzoyloxy group, dimethylbenzoyloxy group, trimethylbenzoyloxy group, ethylbenzoyloxy group and methoxybenzoyloxy group.

The oxycarbonyloxy group of $R^8$ in the general formula (I) means an oxycarbonyloxy group substituted with a hydrocarbon group containing at most 19 carbon atoms.

The hydrocarbon group containing at most 19 carbon atoms in the oxycarbonyloxy group of $R^8$ includes a linear or branched chain hydrocarbon group, a monocyclic hydrocarbon group with or without side chain, a polycyclic hydrocarbon group with or without side chain, a spiro hydrocarbon group with or without side chain, a ring-assembling structural hydrocarbon group with or without side chain, or a chain hydrocarbon group substituted with said cylclic hydrocarbon groups. It includes any saturated or unsaturated hydrocarbon group, provided that unsaturated hydrocarbon groups having allene structure (C=C=C) are excluded. The linear or branched chain hydrocarbon group includes, for example, saturated chain hydrocarbon groups such as a linear alkyl group containing at least one carbon atom and a branched alkyl group containing at least three carbon atoms; unsaturated chain hydrocarbon groups such as a linear alkenyl group containing at least two carbon atoms, a branched alkenyl group containing at least three carbon atoms, a linear alkynyl group containing at least three carbon atoms, a branched alkynyl group containing at least four carbon atoms, a linear alkadienyl group containing at least four carbon atoms and a branched alkadienyl group containing at least five carbon atoms. The monocyclic hydrocarbon group includes, for example, saturated monocyclic hydrocarbon groups such as a cycloalkyl group without side chain which contains at least three carbon atoms and a cycloalkyl group with side chain which contains at least four carbon atoms in total; unsaturated monocyclic hydrocarbon groups such as a cycloalkenyl group without side chain which contains at least four carbon atoms, a cycloalkynyl group with side chain which contains at least five carbon atoms in total, a cycloalkadienyl group without side chain which contains at least five carbon atoms and a cycloalkadienyl group with side chain which contains at least six carbon atoms in total. The aromatic hydrocarbon group includes an aromatic group without side chain which contains at least six carbon atoms in total such as phenyl group, 1-naphthyl group, 2-naphthyl group and 9-anthryl group; an aromatic group with side chain which contains at least seven carbon atoms in total; phenylphenyl group containing 12 carbon atoms and phenylphenyl group with side chain which contains at least 13 carbon atoms in total which phenylphenyl groups are also included in a ring-assembling structural hydrocarbon group. The polycyclic hydrocarbon group includes a condensed cyclic hydrocarbon group without side chain which contains at least six carbon atoms, a condensed cyclic hydrocarbon group with side chain which contains at least seven carbon atoms in total, a bridged cyclic hydrocarbon group without side chain which contains at least seven carbon atoms, a bridged cyclic hydrocarbon group with side chain which contains at least eight carbon atoms in total, a spiro hydrocarbon group without side chain which contains at least nine carbon atoms in total and a spiro hydrocarbon group with side chain which contains at least 10 carbon atoms in total. In addition, said condensed cyclic hydrocarbon group without side chain includes those which contain at least nine carbon atoms in total when one of its condensed rings is benzene ring, and said condensed cyclic hydrocarbon group with side chain includes those which contain at least 10 carbon atoms in total when one of its condensed rings is benzene ring. The ring-assembling structural hydrocarbon group includes a cycloalkyl-cycloalkyl group without side chain which contains at least six carbon atoms in total, a cycloalkyl-cycloalkyl group with side chain which contains at least seven carbon atoms in total, a cycloalkylidene-cycloalkyl group without side chain which contains at least six carbon atoms in total and a cycloalkylidene-cycloalkyl group with side chain which contains at least seven carbon atoms in total. "A cyclic hydrocarbon with side chain" corresponds to one substituted with chain hydrocarbon group or groups on its ring. The chain hydrocarbon group substitute d with said cyclic hydrocarbon groups includes a linear alkyl group which is substituted with an aromatic group without side chain and contains at least seven carbon atoms in total, a linear alkyl group which is substituted with an aromatic group with side chain and contains at least eight carbon atoms in total, a branched alkyl group which is substituted with an aromatic group without side chain and contains at least nine carbon atoms in total, a branched alkyl group which is substituted with an aromatic group with side chain and contains at least 10 carbon atoms in total, a linear alkenyl group which is substituted with an aromatic group without side chain and contains at least eight carbon atoms in total, a linear alkenyl group which is substituted with an aromatic group with side chain and contains at least nine carbon atoms in total, a branched alkenyl group which is substituted with an aromatic group without side chain and contains at least nine carbon atoms in total, a branched alkenyl group which is substituted with an aromatic group with side chain and contains at least 10 carbon atoms in total, a linear alkynyl group which is substituted with an aromatic group without side chain and contains at least eight carbon atoms in total, a linear alkynyl group which is substituted with an aromatic group with side chain and contains at least nine carbon atoms in total, a branched alkynyl group which is substituted with an aromatic group without side chain and contains at least 10 carbon atoms in total, a branched alkynyl group which is substituted with an aromatic group with side chain and contains at least 11 carbon atoms in total, a linear alkadienyl group which is substituted with an aromatic group without side chain and contains at least 10 carbon atoms in total, a linear alkadienyl group which is substituted with an aromatic group with side chain and contains at least 11 carbon atoms in total, a branched alkadienyl group which is substituted with an aromatic group without side chain and contains at least 11 carbon atoms in total, a branched alkadienyl group which is substituted with an aromatic group with side chain and contains at least 12 carbon atoms in total, a linear alkyl group which is substituted with a cycloalkyl group without side chain and contains at least four carbon atoms in total, a linear alkyl group which is substituted with a cycloalkyl group with side chain and contains at least five carbon atoms in total, a branched alkyl group which is substituted with a cycloalkyl group without side chain and contains at least six carbon atoms in total, a branched alkyl group which is substituted with a cycloalkyl group with side chain and contains at least seven carbon atoms in total, a linear alkenyl group which is substituted with a cycloalkyl group without side chain and contains at least five carbon atoms in total, a linear alkenyl group which is substituted with a cycloalkyl group with side chain and contains at least six carbon atoms in total, a branched alkenyl group which is substituted with a cycloalkyl group without side chain and contains at least six carbon atoms in total, a branched alkenyl group which is substituted with a cycloalkyl group with side chain and contains at least seven carbon atoms in total, a linear alkynyl group which is substituted with a cycloalkyl group without side chain and contains at least five carbon atoms in total, a linear alkynyl group which is substituted with a cycloalkyl group with side chain and contains at least six carbon atoms in total, a branched alkynyl group which is substituted with a cycloalkyl group without side chain and contains at least seven carbon atoms in total, a branched alkynyl group which is substituted with a cycloalkyl group with side chain and contains at least eight carbon atoms in total, a branched alkadienyl group which is substituted with a cycloalkyl group without side chain and contains at least eight carbon atoms in total, a branched alkadienyl group which is substituted with a cycloalkyl group with side chain and contains at least nine carbon atoms in total.

When the hydrocarbon group in the oxycarbonyloxy group of $R^8$ is an aromatic group without side chain, an aromatic group with side chain, phenylphenyl group or phenylphenyl group with side chain, it refers to an aryl group, and a linear or branched alkyl group substituted with the aryl group or groups refers to an aralkyl group. Other cyclic hydrocarbon groups including both of one having side chains on their ring and one having no side chain simply refer to, for example, cycloalkyl groups, unless otherwise mentioned. Further, chain hydrocarbon groups including both of linear one and branched one simply refer to, for example, alkyl groups.

Accordingly, the hydrocarbon group containing at most 19 carbon atoms in the oxycarbonyloxy group of $R^8$ may be selected from any chain hydrocarbon group and ring-structural hydrocarbon group such as cyclic hydrocarbon groups, for example, saturated chain hydrocarbon groups such as linear or branched alkyl groups; unsaturated chain hydrocarbon groups such as linear or branched alkenyl groups, linear or branched alkynyl groups and linear or branched alkadienyl groups; saturated cyclic hydrocarbon groups such as cycloalkyl groups; unsaturated cyclic hydrocarbon groups such as cycloalkenyl groups, cycloalkynyl groups and cycloalkadienyl groups; and aromatic hydrocarbon groups such as aryl groups, aralkyl groups and arylalkenyl groups.

In more detail, the linear or branched alkyl groups include methyl group, ethyl group, propyl group, isopropyl group, butyl group, 1-methylpropyl group, pentyl group, 1-methylbutyl group, hexyl group, 1-methylpentyl group, heptyl group, 1-methylhexyl group, 1-ethylpentyl group, octyl group, nonyl group, decyl group, undecyl group, dodecyl group, tridecyl group, tetradecyl group, 2-methylpropyl group, 2-methylbutyl group, 3-methylbutyl group, 2-methylpentyl group, 3-methylpentyl group, 4-methylpentyl group, methylhexyl group, methylheptyl group, methyloctyl group, methylnonyl group, 1,1-dimethylethyl group, 1,1-dimethylpropyl group, 2,6-dimethylheptyl group, 3,7-dimethyloctyl group and 2-ethylhexyl group; cycloalkylalkyl groups include cyclopentylmethyl group and cyclohexylmethyl group; cycloalkyl groups include cyclopropyl group, cyclobutyl group, cyclopentyl group, methylcyclopentyl group, cyclohexyl group, methylcyclohexyl group, cycloheptyl group and cyclooctyl group; and bicycloalkyl groups include norbornyl group, bicyclo[2.2.2]octyl group and adamantyl group.

The linear or branched alkenyl groups include vinyl group, allyl group, crotyl group (2-butenyl group) and isopropenyl group (1-methylvinyl group); cycloalkenyl or cycloalkadienyl groups include cyclopentenyl group, cyclopentadienyl group, cyclohexenyl group and cyclohexadienyl group.

The linear or branched alkynyl groups include ethynyl group, propynyl group and butynyl group. The aryl groups include phenyl group, 1-naphthyl group, 2-naphthyl group, 2-phenylphenyl group, 3-phenylphenyl group, 4-phenylphenyl group, 9-anthryl group, methylphenyl group, dimethylphenyl group, trimethylphenyl group, ethylphenyl group, methylethylphenyl group, diethylphenyl group, propylphenyl group and butylphenyl group.

The aralkyl group include benzyl group, 1-naphthylmethyl group, 2-naphthylmethyl group, phenethyl group (2-phenylethyl group), 1-phenylethyl group, phenylpropyl group, phenylbutyl group, phenylpentyl group, phenylhexyl group, methylbenzyl group, methylphenethyl group, dimethylbenzyl group, dimethylphenethyl group, trimethylbenzyl group, ethylbenzyl group and diethylbenzyl group.

The arylalkenyl groups include styryl group, methylstyryl group, ethylstyryl group, dimethylstyryl group and 3-phenyl-2-propenyl group.

The oxycarbonyloxy group of $R^8$ substituted with a hydrocarbon group containing at most 19 carbon atoms includes methoxycarbonyloxy group, ethoxycarbonyloxy group, propoxycarbonyloxy group, butoxycarbonyloxy group, pentyloxycarbonyloxy group, hexyloxycarbonyloxy group, heptyloxycarbonyloxy group, octyloxycarbonyloxy group, isopropyloxycarbonyloxy group, isobutyloxycarbonyloxy group, tert-butyloxycarbonyloxy group, isopentyloxycarbonyloxy group and benzyloxycarbonyloxy group.

A compound having the acyloxy group or the oxycarbonyloxy group as $R^8$ corresponds to an ester of that having a hydroxyl group as $R^8$, and the ester is a pro-drug of the corresponding compound having a hydroxyl group as $R^8$, which may be improved in solubility, absorption, and in vivo stability. The ester may be metabolized to the corresponding active compound having a hydroxyl group as $R^8$.

A compound represented by the general formula (I) is chemically equivalent with its tautomer, and the purine derivative according to the present invention includes said tautomer. When $R^8$ is a hydroxyl group, for example, a compound of the formula (I) is a hydroxyl derivative represented by the following general formula (II):

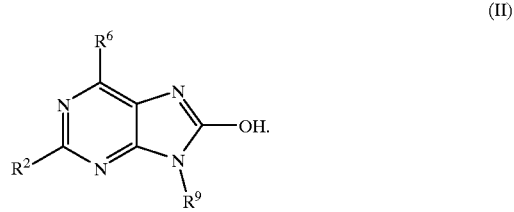

(II)

Its tautomer may be an oxo derivative represented by the following general formula (III):

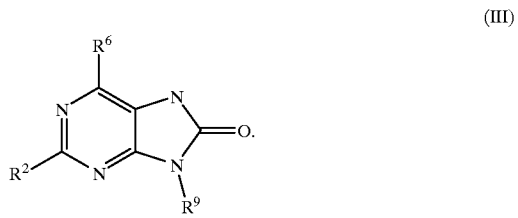

(III)

When $R^6$ is a hydroxyl group, a compound of the formula (I) is a hydroxyl derivative represented by the following general formula (IV):

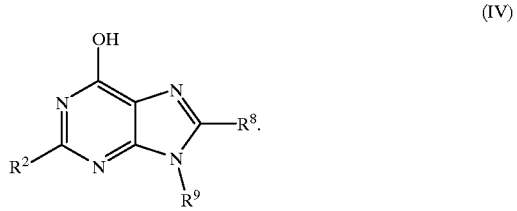

(IV)

Its tautomer may be an oxo derivative represented by the following general formula (V) and (VI):

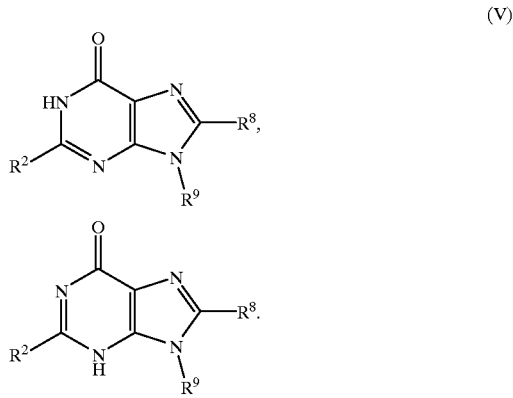

(V)

The preferred embodiments of the present purine derivative include adenine derivatives having an amino group or a mono-substituted or di-substituted amino group as $R^6$, which are represented by the following formulas (VII), (VIII) or (IX):

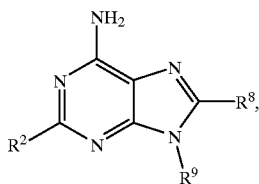

(VII)

wherein R², R⁸ and R⁹ are respectively defined as mentioned in the above formula (I),

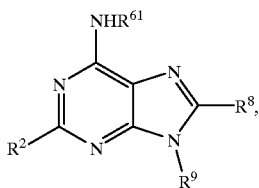

(VIII)

wherein R², R⁸ and R⁹ are respectively defined as mentioned in the above formula (I), and R⁶¹ represents a hydrocarbon group containing at most 10 carbon atoms,

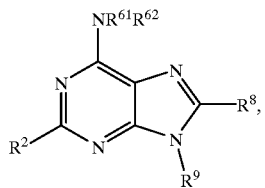

(IX)

wherein R², R⁸ and R⁹ are respectively defined as mentioned in the above formula (I), and R⁶¹ and R⁶² respectively represents a hydrocarbon group containing at most 10 carbon atoms. In particular, adenine derivatives of the general formula (VII) are more preferred. On the other hand, R⁸ are preferably selected from hydroxyl group or mercapto group, more preferably hydroxyl group. Accordingly, 8-hydroxyadenine derivatives of the general formula (X) are more preferred compounds:

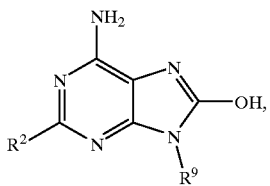

(X)

wherein R² and R⁹ are respectively defined as mentioned in the above formula (I). A compound of the general formula (VII) having an acyloxy group or an oxycarbonyloxy group substituted with a hydrocarbon group as R⁸ corresponds to a pro-drug of the compound represented by the general formula (X).

The preferred embodiments of R² and R⁹ are already mentioned above. More preferably, R⁹ is a non-substituted or substituted benzyl group. Said substituted benzyl group of R⁹ also includes a nitrogen-substituted benzyl group in which an aromatic carbon is replaced with a nitrogen. Substituents on the ring include chain hydrocarbon groups as side chains as well as any structure mentioned above which is derived by the replacement of CH₂ with carbonyl group, sulfonyl group, O or S or the replacement of C—H with N, a C-halogen group or a C—CN group, for example, ketone, aldehyde, carboxylic acid, ester, thioester, amide, carbonate, carbamate, sulfone, sulfonamide, ether, thioether, amine, alcohol, thiol and halogen. Among these structures, halogeno groups, particularly fluoro group, chloro group, bromo group, amino group and halogeno-substituted alkyl groups are more suitable for said substituted benzyl group.

On the other hand, more preferably R² is a non-substituted or substituted hydrocarbon group such as alkyl group, alkenyl group, alkadienyl group, cycloalkyl group, aryl group and aralkyl group. The substituted hydrocarbon groups may contain any structures such as ketone, aldehyde, carboxylic acid, ester, thioester, amide, carbonate, carbamate, sulfone, sulfonamide, ether, thioether, amine, alcohol, thiol and halogen as well as an aromatic ring in which an aromatic carbon is replaced with a nitrogen. Among these groups, non-substituted or substituted lower alkyl groups, non-substituted or substituted benzyl groups and non-substituted or substituted cycloalkylalkyl groups are more suitable as R².

These purine derivatives can be prepared as follows.

(1) R⁸=OH or SH (a) Synthesis of 9-substituted-8-hydroxyadenine derivatives or 9-substituted-8-mercaptoadenine derivatives (Scheme 1)

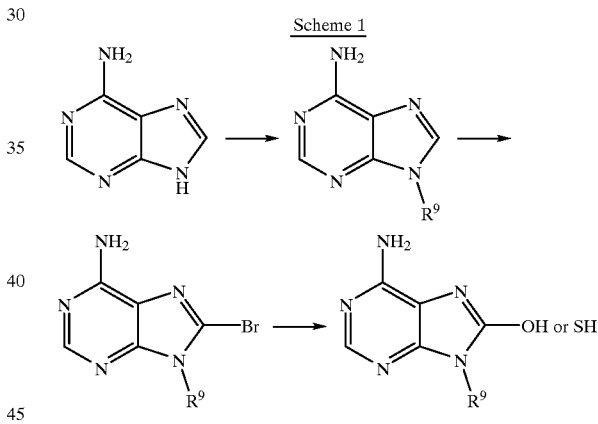

Scheme 1

9-substituted adenine derivatives may be prepared by reacting adenine with a substituted halide R⁹-X, wherein X is a halogen, in the presence of a base such as potassium carbonate, sodium hydroxide or sodium hydride. A reaction solvent may be optionally selected according to the base to be used, for example, dimethylformamide or dimethyl sulfoxide. This reaction may be carried out at a temperature between room temperature and about 80° C. The resulting 9-substituted adenine derivatives may be further reacted with bromine in the presence of a base such as sodium acetate to yield a 9-substituted-8-bromoadenine derivatives. This reaction may be carried out in the presence of a solvent such as acetic acid or chloroform and at a temperature between room temperature and about 100° C. The 9-substituted-8-bromoadenine derivatives may be converted into the desired 9-substituted-8-hydroxyadenine derivatives (R⁸=OH) by reacting it with hydrochloric acid. This reaction may be carried out at a temperature between room temperature and about 100° C, preferably under heating conditions, i.e., at a temperature of about 70 to about 100° C.

On the other hand, 9-substituted-8-mercaptoadenine derivatives ($R^8$=SH) may be prepared by reacting the above 9-substituted-8-bromoadenine derivatives with NaSH. This reaction may be carried out in the presence of a solvent such as alcohols including methanol and ethanol at a temperature between room temperature and reflux temperature of the solvent, preferably under heating conditions.

(b) Synthesis of 2,9-di-substituted-8-hydroxyadenine derivatives or 2,9-di-substituted-8-mercaptoadenine derivatives (Scheme 2)

a temperature between room temperature and about 100° C., preferably under heating conditions. Tertiary amines such as triethylamine may be optionally used as a base.

The resulting 2,9-di-substituted adenine or 2,9-substituted-6N-substituted adenine may be further brominated and then hydrolyzed or reacted with NaSH as described in (a) to yield 2,9-substituted-8-hydroxyadenine, 2,9-substituted-8-mercaptoadenine, 2,9-substituted-6N-substituted-8-hydroxyadenine or 2,9-substituted-6N-substituted-8-mercaptoadenine ($R^6$=amino group or substituted amino group).

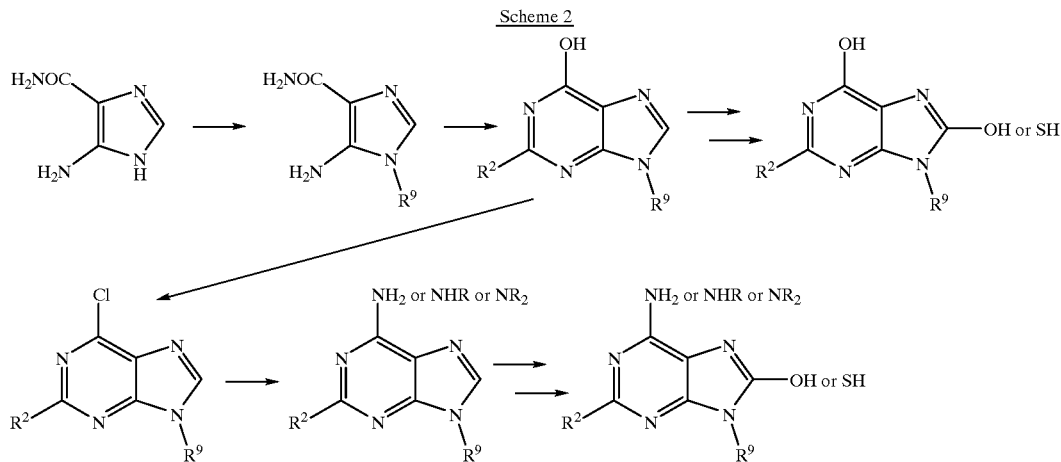

Scheme 2

1-substituted-5-aminoimidazole-4-carboxamide may be prepared by reacting 5-aminoimidazole-4-carboxamide with a substituted halide $R^9$-X, wherein X is a halogen, in the presence of a base such as sodium hydroxide or sodium hydride. A reaction solvent may be optionally selected according to the base to be used, for example, dimethylformamide or dimethyl sulfoxide. This reaction may be carried out at a temperature between room temperature and about 80° C. The resulting 1-substituted-5-aminoimidazole-4-carboxamide may be further reacted with $R^2$-COOEt to yield 2,9-di-substituted hypoxanthine derivatives. This reaction may be carried out in the presence of a base such as sodium ethoxide or sodium methoxide and a solvent such as alcohols including methanol and ethanol and at a temperature between room temperature and reflux temperature of the solvent, preferably under heating conditions.

The resulting 2,9-di-substituted hypoxanthine derivatives may be further brominated and then hydrolyzed or reacted with NaSH as described in (a) to yield 2,9-substituted-8-hydroxyhypoxanthine derivatives or 2,9-substituted-8-mercaptohypoxanthine derivatives ($R^6$=OH).

On the other hand, 2,9-di-substituted-6-chloropurine may be prepared by reacting the above 2,9-di-substituted hypoxanthine derivatives with a chlorinating agent such as phosphorus oxychloride or sulfonyl chloride. This reaction may be carried out in the presence or absence of a solvent such as chloroform and at a temperature between room temperature and about 100° C., preferably under heating conditions. The resulting 2,9-di-substituted-6-chloropurine may be further reacted with ammonia or a mono- or di-substituted amine to yield 2,9-di-substituted adenine or 2,9-substituted-6N-substituted adenine. This reaction may be carried out in the presence of a solvent such as alcohols including ethanol as well as dimethylformamide or dimethyl sulfoxide and at (c) Another synthesis of 2,9-di-substituted-8-hydroxyadenine derivatives or 2,9-di-substituted-8-mercaptoadenine derivatives (Scheme 3)

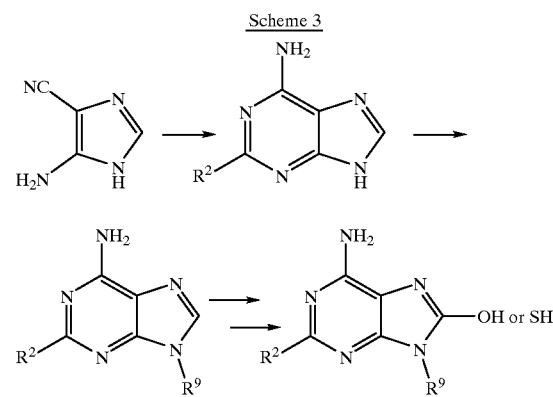

Scheme 3

5-amino-4-cyanoimidazole may be reacted with $R^2CONH_2$ to yield 2-substituted adenine. This reaction may be carried out in molten state without any solvent and preferably at a high temperature of about 150 to about 240° C. The resulting 2-substituted adenine may be further reacted with a substituted halide $R^9$-X, wherein X is a halogen, brominated, and then hydrolyzed or reacted with NaSH as described in (b) to yield 2,9-di-substituted compounds having an amino group as $R^6$.

(d) Another synthesis of 2,9-di-substituted-8-hydroxyadenine derivatives or 2,9-di-substituted-8-mercaptoadenine derivatives (Scheme 4)

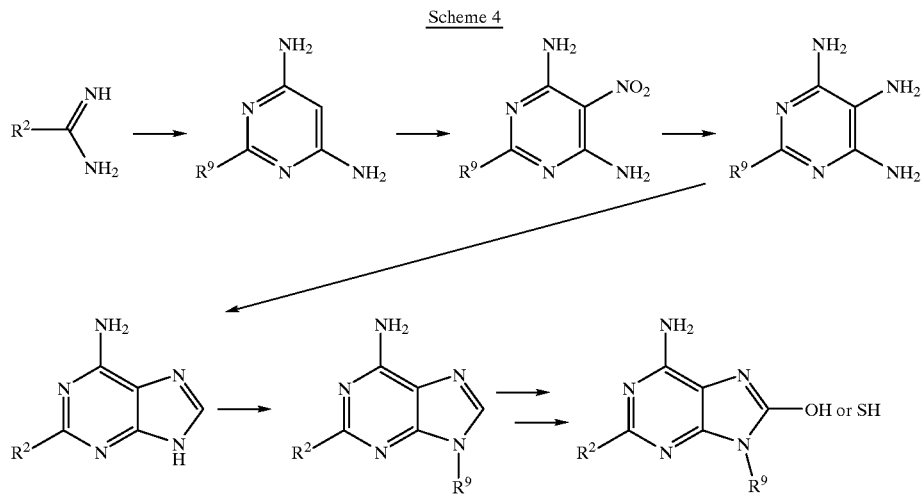

Scheme 4

In addition, other known methods for the formation of purine ring may be also used. For example, an amidine having $R^2$ and malononitrile may be reacted each other to yield pyrimidine derivatives. The resulting pyrimidine derivatives may be further reacted with sodium nitrate or mixed acid to introduce a nitro group into its 5-position and said nitro group may be converted into an amino group by reducing it with Pd/C or Pt/C. The resulting 2-substituted triaminopyrimidine may be further reacted with orthoester to yield 2-substituted adenine. The resulting 2-substituted adenine may be converted into 2,9-di-substituted-8-hydroxyadenine derivatives or 2,9-di-substituted-8-mercaptoadenine derivatives by repeating the procedure of (b).

(2) $R^8$=acyloxy group or alkoxycarbonyloxy group

A purine derivative in which $R^8$ is an acyloxy group or an alkoxycarbonyloxy group may be prepared by reacting the compounds ($R^8$=OH) described in (1) with an acyl chloride or a chloroformate ester $R^8$—Cl in the presence of a base such as triethylamine, diisopropyl-ethylamine or dimethylaminopyridine. This reaction may be carried out in the presence of a solvent such as tetrahydrofuran, 1,4-dioxane or dimethylformamide at a temperature between room temperature and about 80° C.

The present purine derivative thus obtained may be used as pharmaceutically acceptable salts such as sodium salt, potassium salt, hydrochloride, hydrobromide, sulfate, nitrate, acetate, methanesulfonate, toluenesulfonate and citrate.

The interferon inducer according to the present invention may be applied as an oral formulation (capsules, tablets, granule, etc.), injection, or ointment. For example, tablets can be prepared by mixing the present interferon inducer, excipients (lactose, starch, etc.), lubricants (talk, magnesium stearate, etc.) and other conventional additives. Dose of the present interferon inducer should be suitably determined according to sex, age, body weight, disease type and condition of the patient. In general, the present interferon inducer may be administered once or several times a day in a dose of about 0.1 to about 100 mg/kg/day.

BEST MODE FOR CARRYING OUT THE INVENTION

The present invention will be further illustrated by the following examples, which should not be construed to limit the scope of the present invention.

Example 1

9-benzyl-8-hydroxyadenine

A mixture of 8-bromo-9-benzyladenine (760 mg, 2.5 mmol) and conc. HCl was refluxed for 5 h. After cooling, aqueous $NH_3$ was added to neutralize the mixture, and the resulting crystallized compound was collected by filtration (534 mg, Yield: 88.5%).

$^1$H-NMR(DMSO-$d_6$) δ ppm: 4.91 (2H, s), 6.42 (2H, brs), 7.28 (5H, m), 8.01 (1H, s), 10.22 (1H, brs).

mp: 278–280° C.

Anal.: as $C_{12}H_{10}N_5O$ Calcd. C:59.74, H:4.60, N:29.03 Found C:59.56, H:4.54, N:28.84 (%).

Example 2

9-cyclopentyl-8-hydroxyadenine

The desired compound was prepared from 8-bromo-9-cyclopentyladenine by repeating the procedure of Example 1 (Yield: 64%), and it was then re-crystallized in ethanol.

$^1$H-NMR(DMSO-$d_6$) δ ppm: 1.59 (2H, m), 1.86 (4H, m), 2.11 (2H, m), 4.63 (1H, m), 6.35 (2H, s), 7.99 (1H, s), 10.13 (1H, s).

mp: 229–231° C.

Example 3

9-butyl-8-hydroxyadenine

The desired compound was prepared from 8-bromo-9-butyladenine by repeating the procedure of Example 1 (Yield: 63%), and it was then re-crystallized in ethanol.

$^1$H-NMR(DMSO-$d_6$) δ ppm: 0.96 (3H, t, J=7.3 Hz), 1.35 (2H, m), 1.72 (2H, m), 3.78 (2H, t, J=6.8 Hz), 6.46 (2H, s), 8.09 (1H, s), 10.19 (1H, s).

mp: 222–224° C.

Anal.: as $C_9H_{13}N_5O$ Calcd. C:52.16, H:6.32, N:33.79 Found C:52.01, H:6.26, N:33.59 (%).

Example 4

9-(4-fluorobenzyl)-8-hydroxyadenine

The desired compound was prepared from 8-bromo-9-(4-fluorobenzyl)adenine by repeating the procedure of Example 1 (Yield: 80%), and it was then re-crystallized in ethanol.

$^1$H-NMR(DMSO-d$_6$) δ ppm: 4.97 (2H, s), 6.44 (2H, s), 7.23 (4H, m), 8.01 (1H, s), 10.24 (1H, s).

mp: 270–272° C.

Anal.: as C$_{12}$H$_{10}$N$_5$OF.1/5H$_2$O Calcd. C:54.84, H:3.99, N:26.64 Found C:54.97, H:3.87, N:26.38 (%).

Example 5

9-(2-phenylethyl)-8-hydroxyadenine

The desired compound was prepared from 8-bromo-9-(2-phenylethyl)adenine by repeating the procedure of Example 1 (Yield: 81%), and it was then re-crystallized in ethanol.

$^1$H-NMR(DMSO-d$_6$) δ ppm: 3.08 (2H, t), 4.04 (2H, t), 6.47 (2H, s), 7.28 (5H, m), 8.07 (1H, s), 10.19 (1H, s).

mp: 256–258° C.

High Mass: Calcd. 255.1120, Found 255.1116.

Example 6

9-benzyl-6-(N-methylamino)-8-hydroxypurine

The desired compound was prepared from 8-bromo-9-benzyl-6-(N-methylamino) purine by repeating the procedure of Example 1 (Yield: 55%).

$^1$H-NMR(DMSO-d$_6$) δ ppm: 3.03 (3H, s), 4.99 (2H, s), 7.30 (5H, m), 8.32 (1H, s), 8.65 (1H, brs), 11.45 (1H, s).

FAB Mass: 256 (M+H).

Example 7

9-benzyl-8-mercaptoadenine

A mixture of 8-bromo-9-benzyladenine (910 mg, 3.0 mmol), sodium hydrosulfide (1.08 g), and ethanol (50 ml) was refluxed for 12 h. After removal of solvent, the residue was dissolved into water and neutralized by 1 N HCl to obtain the desired compound as crystals (770 mg, Yield: 99%).

TOF-MS: 258 (M+H).

Example 8

9-benzyl-8-methoxycarbonyloxyadenine

Triethylamine (202 mg, 2 mmol) and N,N-dimethylaminopyridine (111 mg 0.5 mmol) were added to 9-benzyl-8-hydroxyadenine (241 mg, 1 mmol) dissolved in anhydrous THF (20 ml). After stirring at room temperature for 1 h, methyl chloroformate (113 mg, 1.2 mmol) was added thereto, and the mixture was stirred overnight at room temperature. The resulting reaction mixture was extracted by ethyl acetate (50 ml) and water (50 ml), and the resulting organic layer was concentrated under vacuum followed by addition of ether (20 ml) to obtain the desired compound as crystals (300 mg, Yield: 100%).

$^1$H-NMR(CDCl$_3$) δ ppm: 4.06 (3H, s), 5.05 (2H, s), 7.33 (5H, m), 8.25 (1H, s).

mp: >300° C.

High Mass: Calcd. 299.1018, Found 299.1006.

Example 9

9-benzyl-8-benzyloxycarbonyloxyadenine

The desired compound was prepared using benzyl chloroformate as an acylating agent corresponding to R$^8$ by repeating the procedure of Example 8 (Yield: 100%).

$^1$H-NMR(CDCl$_3$) δ ppm: 5.04 (2H, s), 5.46 (2H, s), 6.18 (1H, s), 7.41 (10H, m), 8.23 (1H, s).

mp: >300° C.

Anal.: as C$_{20}$H$_{10}$N$_5$O$_3$.1/4H$_2$O Calcd. C:63.23, H:4.64, N:18.43 Found C:63.38, H:4.62, N:18.31 (%).

Example 10

9-benzyl-8-tert-butyloxycarbonyloxyadenine

The desired compound was prepared using di-tert-butyl dicarbonate as an acylating agent corresponding to R$^8$ by repeating the procedure of Example 8 (Yield: 100%).

$^1$H-NMR(CDCl$_3$) δ ppm: 1.73 (9H, s), 5.13 (2H, s), 6.37 (2H, s), 7.45 (5H, m), 8.33 (1H, s).

mp: 287–289° C.

Anal.: as C$_{17}$H$_{19}$N$_5$O$_3$ Calcd. C:59.81, H:5.61, N:20.52 Found C:59.77, H:5.64, N:20.35 (%).

Example 11

9-benzyl-8-acetoxyadenine

The desired compound was prepared using acetyl chloride as an acylating agent corresponding to R$^8$ by repeating the procedure of Example 8 (Yield: 60%).

mp: 189–191° C.

Anal.: as C$_{14}$H$_{13}$N$_5$O$_2$.1/10H$_2$O Calcd. C:58.98, H:4.67, N:24.57 Found C:59.06, H:4.65, N:24.34 (%).

Example 12

9-benzyl-8-benzoyloxyadenine

The desired compound was prepared using benzoyl chloride as an acylating agent corresponding to R$^8$ by repeating the procedure of Example 8 (Yield: 67%).

$^1$H-NMR(CDCl$_3$) δ ppm: 5.03 (2H, s), 5.77 (2H, s), 7.28 (3H, m), 7.48 (4H, m), 7.64 (1H, t, J=7.2 Hz), 7.80 (2H, m), 8.35 (1H, s).

mp: 227–229° C.

Anal.: as C19H$_{15}$N$_5$O$_2$ Calcd. C:66.08, H:4.38, N:20.28 Found C:65.91, H:4.41, N:20.12 (%).

Example 13

9-benzyl-8-(2,2-dimethylpropanoyloxy)adenine

The desired compound was prepared using 2,2-dimethylpropanoyl chloride as an acylating agent corresponding to R$^8$ by repeating the procedure of Example 8 (Yield: 34%).

$^1$H-NMR(CDCl$_3$) δ ppm: 1.59 (9H, s), 5.15 (2H, s), 5.60 (2H, s), 7.48 (5H, m), 8.37 (1H, s).

mp: 202–204° C.

Example 14

9-benzyl-8-pentanoyloxyadenine

The desired compound was prepared using pentanoyl chloride as an acylating agent corresponding to R$^8$ by repeating the procedure of Example 8 (Yield: 100%).

$^1$H-NMR(CDCl$_3$) δ ppm: 0.95 (3H, t, J=7 Hz), 1.42 (2H, m), 1.70 (2H, m), 3.16 (2H, t, J=7 Hz), 5.04 (2H, s), 7.37 (5H, m), 8.24 (1H, s).

mp: 163–165° C.

High Mass: Calcd. 325.1538, Found 325.1525.

Example 15

9-benzyl-8-octanoyloxyadenine

The desired compound was prepared using octanoyl chloride as an acylating agent corresponding to $R^8$ by repeating the procedure of Example 8 (Yield: 100%).

$^1$H-NMR(CDCl$_3$) δ ppm: 0.88 (3H, t), 1.29 (8H, m), 1.72 (2H, m), 3.16 (2H, t), 5.05 (2H, s), 7.38 (5H, m), 8.25 (1H, s).

mp: 248–250° C.

Anal.: as $C_{20}H_{25}N_5O_2 \cdot 1/5H_2O$ Calcd. C:64.74, H:6.90, N:18.87 Found C:64.52, H:6.88, N:18.84(%).

Example 16

9-benzyl-8-octadecanoyloxyadenine

The desired compound was prepared using octadecanoyl chloride as an acylating agent corresponding to $R^8$ by repeating the procedure of Example 8 (Yield: 71%).

$^1$H-NMR(CDCl$_3$) δ ppm: 0.88 (3H, t), 1.25 (28H, m), 1.70 (2H, m), 3.16 (2H, t), 5.05 (2H, s), 7.40 (5H, m), 8.25 (1H, s).

mp: 128–129° C.

High Mass: Calcd. 507.3573, Found 507.3555.

Example 17

Interferon Induction Activity and Cytokine Selectivity

A suspension of a test compound in an aqueous solution of 0.5% CMC-Na was orally administered to Balb/c male mice (100 mg/kg, n=6). Plasma was prepared from blood collected 2 h after administration, and induction of interferon and other cytokines was measured. Plasma interferon was measured by a reported procedure [J. A. Armstrong, methods in Enzymology, 78, 381–7]. Mouse fibloblast L929 (10,000 cells/0.05 ml) were incubated on a 96-well plate for 24 h, and diluted plasma (0.05 ml) was added to the cell culture followed by further incubation for 24 h. Then vesicular stomatitis virus inoculum (0.100 ml) was added to each well, and the cells were dyed by Crystal Violet after incubation for 44 h to observe cytopathic effect. Plasma interferon was measured by dissolving a pigment into 2% aqueous solution of sodium deoxycholate and measuring its absorbance at 595 nm. Plasma TNF-α and IL-6 were measured by using an EIA kit (Amersham). Results are shown in Table 1 in comparison with R-837 (4-amino-1-isobutyl-1H-imidazo[4,5-c]quinoline: EP 145,340). As shown in Table 1, the purine derivative according to the present invention has potent interferon induction activity and high cytokine selectivity.

TABLE 1

| | interferon induction activity | | |
|---|---|---|---|
| Compound | IFN ($10^4$ unit/ml) | TNF-α (ng/ml) | IL-6 (ng/ml) |
| Control | <0.015 | <0.35 | 0.04 ± 0.02 |
| Example 1 | 61 ± 30 | 2.7 ± 0.3 | 0.6 ± 0.1 |
| R-837 | 7 ± 2 | 2.6 ± 1.0 | 1.8 ± 0.5 |

Example 18

Formulation

Tablets were prepared by the general manner according to the following formulation.

| | |
|---|---|
| Compound of Example 1 | 100 mg |
| lactose | 120 mg |
| starch | 30 mg |
| hydroxypropyl cellulose | 5 mg |
| carboxymethyl cellulose-Na | 7 mg |
| magnesium stearate | 0.5 mg |

Example 19

9-benzyl-8-hydroxy-2-methyladenine

K$_2$CO$_3$ (0.26 g, 1.88 mmol) and benzyl bromide (0.5 ml, ca. 2 mmol) were added to a solution of 70 mg (0.47 mmol) of 2-methyladenine in a mixture of DMF (15 ml) and water (5 ml), and stirred at room temperature for 16 h. The solvent was evaporated under vacuum, and the residue was extracted by chloroform. The resulting organic layer was dried over MgSO$_4$, and evaporated under vacuum. 9-Benzyl-2-methyladenine was obtained by the purification of the residue using column chromatography (CH$_2$Cl$_2$:MeOH= 50:1–30:1).

Bromine (0.2 ml) was added to a solution of 9-benzyl-2-methyladenine 60 mg (0.25 mmol) and NaOAc (0.22 g) in AcOH (5 ml), and the mixture was heated at 70° C. for 40 min. The solvent was evaporated under vacuum, and the residue was extracted by EtOAc. The resulting organic layer was evaporated under vacuum, and the residue was purified by column chromatography (CH$_2$Cl$_2$:MeOH=50:1) to obtain 9-benzyl-8-bromo-2-methyladenine as an orange solid (60 mg). A mixture of the resulting 9-benzyl-8-bromo-2-methyladenine (60 mg) and conc.HCl (5 ml) was refluxed for 3 h. After cooling, aqueous NH$_3$ was added to crystallize the product, and the desired compound was collected by filtration (10 mg, Yield: 16%).

$^1$H-NMR(DMSO-d$_6$) δ ppm: 2.31 (3H, s), 4.89 (2H, s), 6.36 (2H, s), 7.24–7.30 (5H, m), 10.09 (1H, s).

TOF-MS: 256(M+1).

Example 20

9-(m-chlorobenzyl)-8-hydroxy-2-methyladenine

The desired compound was prepared using m-chlorobenzyl chloride by repeating the procedure of Example 19 (Yield: 67%).

$^1$H-NMR(DMSO-d$_6$) δ ppm: 2.32 (3H, s), 4.90 (2H, s), 6.38 (2H, s), 7.19–7.35 (4H, m), 10.14 (1H, s).

TOF-MS: 291(M+1).

Example 21

9-benzyl-8-mercapto-2-methyladenine

The desired compound was prepared using 9-benzyl-8-bromo-2-methyladenine by repeating the procedure of Example 7 (Yield: 8%).

$^1$H-NMR(DMSO-d$_6$) δ ppm: 2.36 (3H, s), 5.31 (2H, s), 6.79 (2H, s), 7.27–7.31 (5H, m), 12.30 (1H, s). FAB-MS: 272 (M$^+$).

Example 22

9-benzyl-8-hydroxy-2-pentyladenine

A mixture of 4-amino-5-cyanoimidazole (1.09 g, 11 mmol) and hexaneamide (4.39 g, 38 mmol) was heated at 210° C. for 15 h under $N_2$ atmosphere. After cooling, the residue was dissolved in a mixture of DMF (200 ml) and water (50 ml). Benzyl chloride (3 ml) and $K_2CO_3$ (3 g) was added to the mixture, and heated at 70° C. for 6 h. Solvent was evaporated under vacuum, the residue was extracted by $CH_2Cl_2$. The resulting organic layer was evaporated under vacuum. 9-benzyl-2-pentyladenine was obtained by the purification of the residue by column chromatography ($CH_2Cl_2$:MeOH=100:1–50:1). Bromine (2 ml) was added to the mixture of 9-benzyl- 2-hexyladenine and NaOAc (5 g) in ACOH (40 ml) within an ice bath, and the mixture was heated at 70° C. for 6 h. Solvent was evaporated under vacuum, the residue was extracted by EtOAc. The resulting organic layer was evaporated under vacuum, 9-benzyl-8-bromo-2-pentyladenine was obtained by the purification of the residue by column chromatography ($CH_2Cl_2$:MeOH= 100:1). A mixture of 9-benzyl-8-bromo-2-pentyladenine and conc.HCl (20 ml) was refluxed for 6 h. After cooling, aqueous $NH_3$ was added to neutralize and crystallize the product (pH=8), and the desired compound was collected by filtration (0.25 g, Yield: 8%).

$^1$H-NMR(DMSO-$d_6$) δ ppm: 0.84 (3H, t, J=6.6 Hz), 1.26 (4H, m), 1.65 (2H, m, J=7.2 Hz), 2.55 (2H, t, J=7.2 Hz), 4.88 (2H, s), 6.34 (2H, s), 7.24–7.29 (5H, m), 10.09 (1H, s).

TOF-MS: 312(M+1).

Example 23

9-benzyl-2-cyclohexyl-8-hydroxyadenine

The desired compound was prepared using cyclohexanecarboxamide by repeating the procedure of Example 22 (Yield: 13%).

$^1$H-NMR(DMSO-$d_6$) δ ppm: 1.16–1.85 (11H, m), 4.89 (2H, s), 6.35 (2H, s), 7.23–7.33 (5H, m), 10.14 (1H, s).

TOF-MS: 324(M+1).

Example 24

9-benzyl-8-hydroxy-2-propyladenine

The desired compound was prepared using butaneamide by repeating the procedure of Example 22 (Yield: 66%).

$^1$H-NMR(DMSO-$d_6$) δ ppm: 0.87 (3H, t, J=7.3 Hz), 1.68 (2H, m, J=7.3 Hz), 2.55 (2H, t, J=7.3 Hz), 4.90 (2H, s), 6.35 (2H, s), 7.21–7.30 (5H, m), 10.11 (1H, s).

TOF-MS: 284(M+1).

Example 25

9-benzyl-8-hydroxy-2-phenyl adenine

The desired compound was prepared using benzamide by repeating the procedure of Example 22 (Yield: 11%).

$^1$H-NMR(DMSO-$d_6$) δ ppm: 5.01 (2H, s), 6.52 (2H, s), 7.23–7.44 (8H, m), 8.37 (2H, dd, J=6.0, 1.9 Hz), 10.31 (1H, s).

TOF-MS: 318(M+1).

Example 26

2,9-dibenzyl-8-hydroxyadenine

The desired compound was prepared using 2-phenylacetamide by repeating the procedure of Example 22 (Yield: 52%).

$^1$H-NMR(DMSO-$d_6$) δ ppm: 3.88 (2H, s), 4.89 (2H, s), 6.40 (2H, s), 7.16–7.28 (10H, m), 10.11 (1H, s).

TOF-MS: 332(M+1).

Example 27

2-(1-adamantyl)-9-benzyl-8-hydroxyadenine

The desired compound was prepared using 1-adamantanecarboxamide by repeating the procedure of Example 22 (Yield: 62%).

$^1$H-NMR(DMSO-$d_6$) δ ppm: 1.70 (6H, m), 1.94 (6H, m), 2.02 (3H, m), 4.88 (2H, s), 6.23 (2H, s), 7.24–7.37 (5H, m), 10.11 (1H, s).

TOF-MS: 376(M+1).

Example 28

9-benzyl-8-hydroxy-2-(4-methylphenyl)adenine

The desired compound was prepared using 4-methylbenzamide by repeating the procedure of Example 22 (Yield: 3%).

$^1$H-NMR(DMSO-$d_6$) δ ppm: 2.34 (3H, s), 5.00 (2H, s), 6.49 (2H, s), 7.23–7.40 (7H, m), 8.17 (2H, d, J=7.8 Hz), 10.30 (1H, s).

TOF-MS: 332(M+1).

Example 29

9-benzyl-2-(4-chlorophenyl)-8-hydroxyadenine

The desired compound was prepared using 4-chlorobenzamide by repeating the procedure of Example 22 (Yield: 8%).

$^1$H-NMR(DMSO-$d_6$) δ ppm: 5.01 (2H, s), 6.59 (2H, s), 7.26–7.40 (5H, m), 7.51 (2H, d, J=8.4 Hz), 8.26 (2H, d, J=8.4 Hz), 10.62 (1H, s).

TOF-MS: 353(M+1).

Example 30

9-benzyl-8-hydroxy-2-isobutyladenine

The desired compound was prepared using 3-methylbutaneamide by repeating the procedure of Example 22 (Yield: 34%).

$^1$H-NMR(DMSO-$d_6$) δ ppm: 0.86 (6H, d, J=6.8 Hz), 2.11 (1H, m), 2.45 (2H, d), 4.90 (2H, s), 6.35 (2H, s), 7.24–7.31 (5H, m).

TOF-MS: 298(M+1).

Example 31

9-(2,4-dichlorobenzyl)-8-hydroxy-2-methyladenine

The desired compound was prepared using 2,4-dichlorobenzyl chloride by repeating the procedure of Example 19 (Yield: 31%).

$^1$H-NMR(DMSO-$d_6$) δ ppm: 2.22 (3H, s), 4.93 (2H, s), 6.42 (2H, s), 6.96 (1H, d, J=8.1 Hz), 7.35 (1H, d, J=8.1 Hz), 6.67 (1H, s), 10.09 (1H, s).

TOF-MS: 325(M+1).

Example 32

9-benzyl-8-hydroxy-2-hydroxymethyladenine

The desired compound was prepared using benzyloxyacetamide by repeating the procedure of Example 22 (Yield: 6%).

Example 33

9-isobutyl-8-hydroxy-2-methyladenine

The desired compound was prepared using isobutyl chloride by repeating the procedure of Example 19 (Yield: 20%).

$^1$H-NMR(DMSO-$d_6$) δ ppm: 0.84 (6H, d, J=6.6 Hz), 2.15 (1H, 7, J=6.6 Hz), 3.50 (2H, d, J=7.2 Hz), 6.30 (2H, s), 9.99 (1H, s).

TOF-MS: 222(M+1).

Example 34

9-benzyl-2-tert-butyl-8-hydroxyadenine

The desired compound was prepared using 2,2-dimethylpropaneamide by repeating the procedure of Example 22 (Yield: 3%).

$^1$H-NMR(DMSO-$d_6$) δ ppm: 1.27 (9H, s), 4.88 (2H, s), 6.25 (2H, s), 7.22–7.38 (5H, m), 10.01 (1H, s).

TOF-MS: 298(M+1).

Example 35

9-benzyl-2-heptyl-8-hydroxyadenine

The desired compound was prepared using octanamide by repeating the procedure of Example 22 (Yield: 19%).

$^1$H-NMR(DMSO-$d_6$) δ ppm: 0.84 (3H, t, J=7.5 Hz), 1.22–1.24 (8H, m), 1.62–1.67 (2H, m), 2.56 (3H, t, J=7.5 Hz), 4.89 (2H, s,), 6.33 (2H, s), 7.24–7.29 (5H, m), 10.08 (1H, s).

TOF-MS: 340(M+1).

Example 36

9-(2-chlorobenzyl)-8-hydroxy-2-methyladenine

The desired compound was prepared using 2-chlorobenzyl chloride by repeating the procedure of Example 19 (Yield: 30%).

$^1$H-NMR(DMSO-$d_6$) δ ppm: 2.28 (3H, s), 4.96 (2H, s), 6.42 (2H, s), 6.89 (1H, d), 7.23–7.32 (2H, m), 7.50 (1H, d), 10.20 (1H, s).

TOF-MS: 291(M+1).

Example 37

9-(4-chlorobenzyl)-8-hydroxy-2-methyladenine

The desired compound was prepared using 4-chlorobenzyl chloride by repeating the procedure of Example 19 (Yield: 42%).

$^1$H-NMR(DMSO-$d_6$) δ ppm: 2.31 (3H, s), 4.89 (2H, s), 6.37 (2H, s), 7.28 (2H, d), 7.38 (2H, d), 10.11 (1H, s).

TOF-MS: 291(M+1).

Example 38

9-(3-bromobenzyl)-8-hydroxy-2-methyladenine

The desired compound was prepared using 3-bromobenzyl chloride by repeating the procedure of Example 19 (Yield: 59%).

$^1$H-NMR(DMSO-$d_6$) δ ppm: 2.33 (3H, s), 4.90 (2H, s), 6.35 (2H, s), 7.14–7.38 (4H, m), 10.16 (1H, s).

TOF-MS: 335(M+1).

Example 39

8-hydroxy-2-methyl-9-(4-methylbenzyl)adenine

The desired compound was prepared using 4-methylbenzyl chloride by repeating the procedure of Example 19 (Yield: 62%).

$^1$H-NMR(DMSO-$d_6$) δ ppm: 2.26 (3H, s), 2.33 (3H, s), 4.90 (2H, s), 6.38 (2H, s), 7.14 (2H, d), 7.22 (2H, d), 10.14 (1H, s).

TOF-MS: 270(M+1).

Example 40

8-hydroxy-2-methyl-9-(4-methoxybenzyl)adenine

The desired compound was prepared using 4-methoxybenzyl chloride by repeating the procedure of Example 19 (Yield: 52%).

$^1$H-NMR(DMSO-$d_6$) δ ppm: 2.26 (3H, s), 3.72 (3H, s), 4.88 (2H, s), 6.39 (2H, s), 6.90 (2H, d), 7.31 (2H, d), 10.14 (1H, s).

TOF-MS: 286(M+1).

Example 41

9-(4-tert-butylbenzyl)-8-hydroxy-2-methyladenine

The desired compound was prepared using 4-tert-butylbenzyl chloride by repeating the procedure of Example 19 (Yield: 57%).

$^1$H-NMR(DMSO-$d_6$) δ ppm: 1.23 (9H, s), 2.28 (3H, s), 4.89 (2H, s), 6.40 (2H, s), 7.25 (2H, d), 7.36 (2H, d), 10.15 (1H, s).

TOF-MS: 312(M+1).

Example 42

8-hydroxy-2-methyl-9-(α-methylbenzyl)adenine

The desired compound was prepared using α-methylbenzyl chloride by repeating the procedure of Example 19 (Yield: 69%).

$^1$H-NMR(DMSO-$d_6$) δ ppm: 1.95 (3H, d), 2.28 (3H, s), 4.89 (2H, s), 5.81 (1H, m), 6.39 (2H, s), 7.25–7.36 (5H, m), 10.13 (1H, s).

TOF-MS: 270(M+1).

Example 43

8-hydroxy-2-methyl-9-(1-naphthylmethyl)adenine

The desired compound was prepared using 1-naphthylmethyl chloride by repeating the procedure of Example 19 (Yield: 52%).

$^1$H-NMR(DMSO-$d_6$) δ ppm: 2.28 (3H, s), 5.42 (2H, s), 6.39 (2H, s), 7.20–8.01 (7H, m), 10.15 (1H, s).

TOF-MS: 306(M+1).

Example 44

8-hydroxy-2-methyl-9-(2-naphthylmethyl)adenine

The desired compound was prepared using 2-naphthylmethyl chloride by repeating the procedure of Example 19 (Yield: 67%).

¹H-NMR(DMSO-d₆) δ ppm: 2.29 (3H, s), 5.22 (2H, s), 6.39 (2H, s), 7.49–7.88 (7H, m), 10.12 (1H, s).
TOF-MS: 306(M+1).

Example 45

8-hydroxy-2-methyl-9-(3-trifluoromethylbenzyl) adenine

The desired compound was prepared using 3-trifluoromethylbenzyl chloride by repeating the procedure of Example 19 (Yield: 72%).
¹H-NMR(DMSO-d₆) δ ppm: 2.28 (3H, s), 5.12 (2H, s), 6.38 (2H, s), 7.57–7.76 (4H, m), 10.15 (1H, s).
TOF-MS: 324(M+1).

Example 46

9-(2,3-dichlorobenzyl)-8-hydroxy-2-methyladenine

The desired compound was prepared using 2,3-dichlorobenzyl chloride by repeating the procedure of Example 19 (Yield: 60%).
¹H-NMR(DMSO-d₆) δ ppm: 2.28 (3H, s), 5.15 (2H, s), 6.39 (2H, s), 6.99 (1H, m), 7.32 (1H, m), 7.61 (1H, m), 10.13 (1H, s).
TOF-MS: 325(M+1).

Example 47

9-benzyl-8-hydroxy-2-isopropyladenine

The desired compound was prepared using 2-methylpropaneamide by repeating the procedure of Example 22 (Yield: 14%).
¹H-NMR(DMSO-d₆) δ ppm: 1.51 (6H, d), 2.15 (1H, m), 4.89 (2H, s), 6.39 (2H, s), 7.41 (5H, m), 10.13 (1H, s).
TOF-MS: 284(M+1).

Example 48

8-hydroxy-2-methyl-9-(3-pyridylmethyl)adenine

The desired compound was prepared using 3-pyridylmethyl chloride by repeating the procedure of Example 19 (Yield: 25%).
¹H-NMR(DMSO-d₆) δ ppm: 2.35 (3H, s), 4.93 (2H, s), 6.42 (2H, s), 7.17 (1H, d), 7.27–7.32 (1H, m), 7.29–7.79 (1H, m), 8.48 (1H, d), 10.15 (1H, s).
TOF-MS: 256(M+1).

Example 49

8-hydroxy-2-methyl 9-(2-pyridylmethyl)adenine

The desired compound was prepared using 2-pyridylmethyl chloride by repeating the procedure of Example 19 (Yield: 24%).
¹H-NMR(DMSO-d₆) δ ppm: 2.31 (3H, s), 4.95 (2H, s), 6.42 (2H, s), 7.20 (1H, d), 7.28 (1H, dd), 7.79 (1H, dd), 8.48 (1H, d), 10.10 (1H, s).
TOF-MS: 256(M+1).

Example 50

8-hydroxy-2-methyl-9-(4-pyridylmethyl)adenine

The desired compound was prepared using 4-pyridylmethyl chloride by repeating the procedure of Example 19 (Yield: 31%).

¹H-NMR(DMSO-d₆) δ ppm: 2.30 (3H, s), 4.98 (2H, s), 6.42 (2H, s), 7.20 (2H, d), 8.54 (2H, d), 10.18 (1H, s).
TOF-MS: 256(M+1).

Example 51

9-benzyl-8-hydroxy-2-(3-pyridyl)adenine

The desired compound was prepared using nicotinamide by repeating the procedure of Example 22 (Yield: 11%).
¹H-NMR(DMSO-d₆) δ ppm: 4.87 (2H, s), 6.40 (2H, s), 7.27–7.36 (5H, m), 7.57 (1H, dd), 8.40 (1H, d), 8.71 (1H, d), 9.19 (1H, s), 10.17 (1H, s).
TOF-MS: 318(M+1).

Example 52

9-benzyl-8-hydroxy-2-(1-naphthylmethyl)adenine

The desired compound was prepared using 2-(naphthalene-1-yl) acetamide by repeating the procedure of Example 22 (Yield: 22%).
¹H-NMR(DMSO-d₆) δ ppm: 3.89 (2H, s), 5.42 (2H, s), 6.39 (2H, s), 7.18–8.05 (12H, m), 10.15 (1H, s).
TOF-MS: 382(M+1).

Example 53

9-benzyl-8-hydroxy-2-(2-naphthylmethyl)adenine

The desired compound was prepared using 2-(naphthalene-2-yl) acetamide by repeating the procedure of Example 22 (Yield: 34%).
¹H-NMR(DMSO-d₆) δ ppm: 3.95 (2H, s), 5.20 (2H, s), 6.41 (2H, s), 7.49–7.90 (12H, m), 10.14 (1H, s).
TOF-MS: 382(M+1).

Example 54

9-benzyl-2-cyclopropyl-8-hydroxyadenine

The desired compound was prepared using cyclopropane-carboxamide by repeating the procedure of Example 22 (Yield: 9%).
¹H-NMR(DMSO-d₆) δ ppm: 0.84–0.96 (4H, m), 1.94–1.99 (1H, m), 4.88 (2H, s), 6.40 (2H, s), 7.38 (5H, m), 10.16 (1H, s).
TOF-MS: 282(M+1).

Example 55

9-benzyl-8-hydroxy-2-(2-pyridylmethyl)adenine

The desired compound was prepared using 2-(pyridine-2-yl) acetamide by repeating the procedure of Example 22 (Yield: 16%).
¹H-NMR(DMSO-d₆) δ ppm: 3.75 (2H, s), 4.87 (2H, s), 6.42 (2H, s), 7.24 (1H, d), 7.28–7.59 (6H, m), 7.79 (1H, dd), 8.51 (1H, d), 10.10 (1H, s).
TOF-MS: 333(M+1).

Example 56

9-benzyl-8-hydroxy-2-(3-pyridylmethyl)adenine

The desired compound was prepared using 2-(pyridine-3-yl) acetamide by repeating the procedure of Example 22 (Yield: 21%).

$^1$H-NMR(DMSO-d$_6$) δ ppm: 3.88 (2H, s), 4.87 (2H, s), 6.42 (2H, s), 7.20–7.55 (8H, m), 8.52 (1H, d), 10.09 (1H, s).

TOF-MS: 333(M+1).

Example 57

9-benzyl-8-hydroxy-2-(4-pyridylmethyl)adenine

The desired compound was prepared using 2-(pyridine-4-yl) acetamide by repeating the procedure of Example 22 (Yield: 32%).

$^1$H-NMR(DMSO-d$_6$) δ ppm: 3.92 (2H, s), 4.87 (2H, s), 6.41 (2H, s), 7.19–7.54 (7H, m), 8.52 (2H, d), 10.10 (1H, s).

TOF-MS: 333(M+1).

Example 58

9-(4-aminobenzyl)-8-hydroxy-2-methyladenine 9-(4-Nitrobenzyl)-2-methyl-8-hydroxyadenine was prepared using 4-nitrobenzyl chloride by repeating the procedure of Example 22 (Yield: 36%). A mixture of 9-(4-nitrobenzyl)-2-methyl-8-hydroxyadenine (300 mg) and 5% Pd/C (30 mg) in EtOH (30 ml) was stirred under H$_2$ atmosphere for 24 h. Insolubles were removed by filtration and the filtrate was evaporated under vacuum to obtain the desired compound (Yield 74%).

$^1$H-NMR(DMSO-d$_6$) δ ppm: 2.30 (3H, s), 4.99 (2H, s), 6.41 (2H, s), 6.83 (2H, s), 7.30 (2H, d), 7.40 (2H, d), 10.14 (1H, s).

TOF-MS: 271(M+1).

Example 59

IFN Induction in Human Peripheral Blood Mononuclear Cells (PBMC) Cultures In Vitro Human whole blood was obtained from healthy volunteers using heparin vacutainer tubes. Peripheral blood mononuclear cells (PBMC) were isolated using Lymphoprep™ (NYCOMED PHARMA AS) by density gradient centrifugation. The PBMC were washed twice with serum free RPMI 1640 medium. Then cell suspension (1×10$^6$/ml) was prepared by adding RPMI 1640 medium containing 10% fetal bovine serum, and incubated for 24 hours at 37° C. under 5% CO$_2$ atmosphere with test compounds dissolved in dimethyl sulfoxide (final conc. 0.1%). For control culture, 0.1% dimethyl sulfoxide without test compounds was used. Culture medium was collected by aseptic filtration, and store at a temperature below −20° C. until measuring IFN-α. Human IFN-α level in the culture medium was determined using high sensitive interferon-α ELISA system (Amersham). Results are shown in Table 2 in comparison with R-837 (4-amino-1-isobutyl-1H-imidazo[4,5-c] quinoline: EP 145,340). As shown in the table 2, the purine derivative according to the present invention has potent interferon induction activity.

TABLE 2 interferon induction activity

| Compound | IFN (pg/ml) | |
|---|---|---|
| | 1 μM | 10 μM |
| Example 19 | 1.7 | 26.5 |
| Example 20 | 15.6 | 38.6 |
| Example 21 | <0.6 | 14.6 |
| Example 22 | 22.8 | 52.8 |
| Example 26 | 14.9 | 33.0 |
| R-837 | 0.8 | 16.7 |

INDUSTRIAL APPLICABILITY

The present purine derivatives having a specific structure show selective and potent activity of interferon induction. The present purine derivatives can promote in vivo secretion of interferon and therefore useful for treatment of cancer and viral diseases such as type B and type C hepatitis and AIDS, against which diseases interferon is effective. In addition, the present purine derivatives can be orally administered and have no antigenicity because of their low-molecular weight.

We claim:

1. A purine derivative represented by the following formula (Ia):

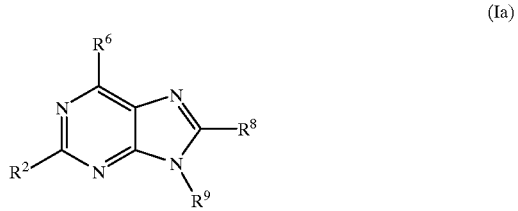

wherein

R$^2$ is a hydrocarbon group containing at most 14 carbon atoms; any —CH$_2$— group in said hydrocarbon group may be replaced with a carbonyl group, a sulfonyl group —O— or —S— when said —CH$_2$— group is not directly attached to the purine ring or is in —CH$_3$ group not directly attached to the purine ring: any =CH$_2$ group may be replaced with =O or =S; C—H group in said hydrocarbon group may be replaced with N, a C-halogen group or a C—CN group when said C—H group is in —CH$_2$— group not directly attached to the purine ring, in —CH$_3$ group not directly attached to the purine ring, in >CH— group not directly attached to the purine ring, in =CH— group not directly attached to the purine ring or in =CH$_2$ group;

R$^6$ is an amino group;

R$^8$ is a hydroxyl group, a mercapto group, a group of the formula:

wherein R$^{10}$ is a hydrogen atom or a hydrocarbon group containing at most 17 carbon atoms, or an oxycarbonyloxy group substituted with a hydrocarbon group containing at most 19 carbon atoms;

R$^9$ is a hydrocarbon group containing at most 14 carbon atoms; any —CH$_2$— group in said R$^9$ may be replaced with a carbonyl group, a sulfonyl group, —O— or —S— when said —CH$_2$— group is not directly attached to the purine ring or is in —CH$_3$ group not directly attached to the purine ring; any ═CH$_2$ group may be replaced with ═O or ═S; C—H group in said R$^9$ may be replaced with a C-halogen group or a C—CN group when said C—H group is in —CH$_2$— group not directly attached to the purine ring, in —CH$_3$ group not directly attached to the purine ring, in >CH— group not directly attached to the purine ring, in ═CH— group not directly attached to the purine ring, in ═CH$_2$ group or in ≡CH group;

or its tautomer or pharmaceutically acceptable salts thereof.

2. A method for inducing α-interferon in a patient having Hepatitis B or C, comprising:

administering to said patient an effective amount of a purine derivative represented by formula (I):

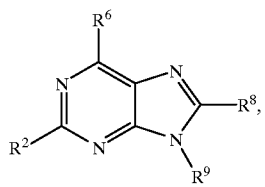

(I)

wherein

R$^2$ is a hydrocarbon group containing at most 14 carbon atoms; any —CH$_2$— group in said hydrocarbon group may be replaced with a carbonyl group, a sulfonyl group, —O— or —S— when said —CH$_2$— group is not directly attached to the purine ring or is in —CH$_3$ group not directly attached to the purine ring; any ═CH$_2$ group may be replaced with ═O or ═S; C—H group in said hydrocarbon group may be replaced with N, a C-halogen group or a C—CN group when said C—H group is in —CH$_2$— group not directly attached to the purine ring, in —CH$_3$ group not directly attached to the purine ring, in >CH— group not directly attached to the purine ring, in ═CH— group not directly attached to the purine ring or in ═CH$_2$ group;

R$^6$ is an amino group;

R$^8$ is a hydroxyl group, a mercapto group, a group of the formula:

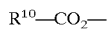

R$^{10}$—CO$_2$— wherein R$^{10}$ is a hydrogen atom or a hydrocarbon group containing at most 17 carbon atoms, or an oxycarbonyloxy group substituted with a hydrocarbon group containing at most 19 carbon atoms;

R$^9$ is a hydrocarbon group containing at most 14 carbon atoms; any —CH$_2$— group in said R$^9$ may be replaced with a carbonyl group, a sulfonyl group, —O— or —S— when said —CH$_2$— group is not directly attached to the purine ring or is in —CH$_3$ group not directly attached to the purine ring; any ═CH$_2$ group may be replaced with ═O or ═S; C—H group in said R$^9$ may be replaced with a C-halogen group or a C—CN group when said C—H group is in —CH$_2$— group not directly attached to the purine ring, in —CH$_3$ group not directly attached to the purine ring, in >CH— group not directly attached to the purine ring, in ═CH— group not directly attached to the purine ring, in ═CH$_2$ group or in ≡CH group;

or its tautomer or pharmaceutically acceptable salts thereof, effective to treat said patient having Hepatitis B or C.

3. A compound according to claim 1, wherein R$^8$ is a hydroxyl group.

4. A compound according to claim 1, wherein R$^9$ is a non-substituted benzyl group or a benzyl group substituted on the aromatic ring with a substituent or substituents selected from halogen groups and lower alkyl groups.

5. A method for promoting a secretion of α-interferon in a cell capable of secreting α-interferon, comprising administering an amount of a purine derivative represented by formula (I) to said cell:

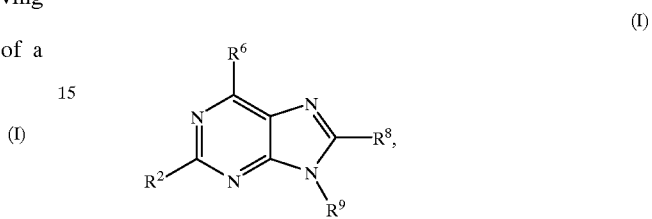

(I)

wherein

R$^2$ is a hydrocarbon group containing at most 14 carbon atoms; any —CH$_2$— group in said hydrocarbon group may be replaced with a carbonyl group, a sulfonyl group, —O— or —S— when said —CH$_2$— group is not directly attached to the purine ring or is in —CH$_3$ group not directly attached to the purine ring; any ═CH$_2$ group may be replaced with ═O or ═S; C—H group in said hydrocarbon group may be replaced with N, a C-halogen group or a C—CN group when said C—H group is in —CH$_2$— group not directly attached to the purine ring, in —CH$_3$ group not directly attached to the purine ring, in >CH— group not directly attached to the purine ring, in ═CH— group not directly attached to the purine ring or in ═CH$_2$ group;

R$^6$ is an amino group;

R$^8$ is a hydroxyl group, a mercapto group, a group of the formula:

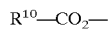

R$^{10}$—CO$_2$— wherein R$^{10}$ is a hydrogen atom or a hydrocarbon group containing at most 17 carbon atoms, or an oxycarbonyloxy group substituted with a hydrocarbon group containing at most 19 carbon atoms;

R$^9$ is a hydrocarbon group containing at most 14 carbon atoms; any —CH$_2$— group in said R$^9$ may be replaced with a carbonyl group a sulfonyl group, —O— or —S— when said —CH$_2$— group is not directly attached to the purine ring or is in —CH$_3$ group not directly attached to the purine ring; any ═CH$_2$ group may be replaced with ═O or ═S; C—H group in said R$^9$ may be replaced with a C-halogen group or a C—CN group when said C—H group is in —CH$_2$— group not directly attached to the purine ring, in —CH$_3$ group not directly attached to the purine ring, in >CH— group not directly attached to the purine ring, in ═CH— group not directly attached to the purine ring, in ═CH$_2$ group or in ≡CH group;

or its tautomer or pharmaceutically acceptable salts thereof, effective to promote a secretion of interferon in said cell.

* * * * *

UNITED STATES PATENT AND TRADEMARK OFFICE
CERTIFICATE OF CORRECTION

PATENT NO. : 6,028,076
DATED : February 22, 2000
INVENTOR(S): Kohsaku HIROTA, ET AL.

It is certified that an error appears in the above-identified patent and that said Letters Patent is hereby corrected as shown below:

Column 42, line 43 "group -O-" should read --group, -O- --.

Column 42, line 45 "ring:" should read --ring;--.

Column 43, line 49 "atoms," should read --atoms;--.

Column 44, line 50 "carbonyl group" should read --carbonyl group,--.

Signed and Sealed this

Seventeenth Day of April, 2001

Attest:

NICHOLAS P. GODICI

Attesting Officer    Acting Director of the United States Patent and Trademark Office